(12) United States Patent
Yoon et al.

(10) Patent No.: US 12,215,066 B2
(45) Date of Patent: Feb. 4, 2025

(54) ORGANIC PHOTODETECTOR AND ELECTRONIC DEVICE INCLUDING THE SAME

(71) Applicant: Samsung Display Co., Ltd., Yongin-si (KR)

(72) Inventors: Seokgyu Yoon, Yongin-si (KR); Dongkyu Seo, Yongin-si (KR); Junyong Shin, Yongin-si (KR); Byeongwook Yoo, Yongin-si (KR); Daeho Lee, Yongin-si (KR); Byungseok Lee, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 416 days.

(21) Appl. No.: 17/674,751

(22) Filed: Feb. 17, 2022

(65) Prior Publication Data
US 2022/0402859 A1    Dec. 22, 2022

(30) Foreign Application Priority Data
Jun. 1, 2021   (KR) .................. 10-2021-0070964

(51) Int. Cl.
*H01L 29/08* (2006.01)
*C07C 209/86* (2006.01)
(Continued)

(52) U.S. Cl.
CPC .......... *C07C 209/86* (2013.01); *C07C 211/49* (2013.01); *C07C 211/57* (2013.01);
(Continued)

(58) Field of Classification Search
CPC ................ C07C 209/86; C07C 211/49; C07C 211/57; C07C 211/61; H10K 30/81; H10K 30/20;
(Continued)

(56) References Cited

U.S. PATENT DOCUMENTS

| 8,101,950 B2 | 1/2012 | Yamazaki et al. |
| 2010/0132770 A1* | 6/2010 | Beatty .................... H10K 30/35 257/E51.012 |

(Continued)

FOREIGN PATENT DOCUMENTS

| KR | 10-1100717 | 12/2011 |
| KR | 10-1418459 | 7/2014 |

(Continued)

OTHER PUBLICATIONS

Kamada, Taisuke, et al. "OLED Display Incorporating Organic Photodiodes for Fingerprint Imaging." Journal of the Society for Information Display, vol. 27, No. 6, 2019, pp. 361-371.

*Primary Examiner* — Niki H Nguyen
(74) *Attorney, Agent, or Firm* — KILE PARK REED & HOUTTEMAN PLLC

(57) ABSTRACT

An organic photodetector includes: a first electrode; a second electrode facing the first electrode; an activation layer between the first electrode and the second electrode; a hole injection layer between the first electrode and the activation layer; and a hole transport layer between the hole injection layer and the activation layer, wherein the hole transport layer includes: a first hole transport layer including a p-dopant; and a second hole transport layer not including a p-dopant.

20 Claims, 4 Drawing Sheets

(51) Int. Cl.

| | |
|---|---|
| C07C 211/49 | (2006.01) |
| C07C 211/57 | (2006.01) |
| C07C 211/61 | (2006.01) |
| C07D 235/18 | (2006.01) |
| C07D 239/26 | (2006.01) |
| C07D 249/08 | (2006.01) |
| C07D 251/24 | (2006.01) |
| C07D 307/91 | (2006.01) |
| C07D 401/04 | (2006.01) |
| C07D 401/12 | (2006.01) |
| C07D 401/14 | (2006.01) |
| C07D 403/14 | (2006.01) |
| C07D 405/12 | (2006.01) |
| C07D 409/12 | (2006.01) |
| C07D 471/04 | (2006.01) |
| C07D 487/14 | (2006.01) |
| C07F 5/06 | (2006.01) |
| H10K 30/20 | (2023.01) |
| H10K 30/81 | (2023.01) |
| H10K 65/00 | (2023.01) |
| H10K 85/20 | (2023.01) |

(52) U.S. Cl.
CPC .......... *C07C 211/61* (2013.01); *C07D 235/18* (2013.01); *C07D 239/26* (2013.01); *C07D 249/08* (2013.01); *C07D 251/24* (2013.01); *C07D 307/91* (2013.01); *C07D 401/04* (2013.01); *C07D 401/12* (2013.01); *C07D 401/14* (2013.01); *C07D 403/14* (2013.01); *C07D 405/12* (2013.01); *C07D 409/12* (2013.01); *C07D 471/04* (2013.01); *C07D 487/14* (2013.01); *C07F 5/069* (2013.01); *H10K 30/20* (2023.02); *H10K 30/81* (2023.02); *H10K 65/00* (2023.02); *H10K 85/211* (2023.02)

(58) Field of Classification Search
CPC ...... H10K 85/211; H10K 65/00; H10K 50/15; H10K 50/16; H10K 50/13; H10K 50/171; H10K 50/156; H10K 50/155; H10K 50/131; H10K 59/12; H10K 50/81; H10K 50/00; H10K 50/805; H10K 59/38; H10K 50/166; H10K 50/115; H10K 2102/00; H10K 71/30; H10K 59/122; H10K 59/10; H10K 50/30; H10K 2102/311; H10K 59/805; H10K 59/352; H10K 50/10; H10K 2102/302; H10K 59/40; H10K 2102/3031; H10K 59/86; H10K 2102/301; H10K 59/65; H10K 59/84; H10K 2102/3023; H10K 59/50; H10K 50/182; H10K 59/60; H10K 59/70; C07D 235/18; C07D 239/26; C07D 249/08; C07D 241/24; C07D 307/91; C07D 401/04; C07D 401/12; C07D 401/14; C07D 405/12; C07D 471/04; C07D 487/14; C07F 5/069

See application file for complete search history.

(56) References Cited

U.S. PATENT DOCUMENTS

| | | | |
|---|---|---|---|
| 2016/0133850 A1* | 5/2016 | Matsuura | ............. C07D 403/10 257/40 |
| 2019/0172872 A1* | 6/2019 | Tsutsumi | .......... H01L 27/14667 |
| 2019/0296256 A1 | 9/2019 | Kim et al. | |

FOREIGN PATENT DOCUMENTS

| | | |
|---|---|---|
| KR | 10-2019-0112373 | 10/2019 |
| KR | 10-2094141 | 3/2020 |

* cited by examiner

ORGANIC PHOTODETECTOR AND ELECTRONIC DEVICE INCLUDING THE SAME

CROSS-REFERENCE TO RELATED APPLICATION

This application claims priority from and the benefit of Korean Patent Application No. 10-2021-0070964, filed on Jun. 1, 2021, which is hereby incorporated by reference for all purposes as if fully set forth herein.

BACKGROUND

Field

Embodiments of the invention relate generally to display devices, and more particularly, to an organic photodetector and an electronic apparatus including the same.

Discussion of the Background

Photoelectric devices, which are elements that convert light into electrical signals, include a photodiode and a phototransistor, and are applicable to image sensors, solar cells, organic light-emitting devices, and the like. In the case of silicon used mostly in photodiodes, a reduction in sensitivity may occur, due to the absorption area becoming smaller with smaller pixel sizes. Accordingly, organic materials that can replace silicon are being studied. Organic materials have a large absorption coefficient and can selectively absorb light of specific wavelength ranges according to molecular structures, and thus can replace a photodiode and a color filter at the same time, and are very advantageous in terms of sensitivity improvement and high integration. Organic photodetectors (OPDs) including such organic materials are applicable to, for example, display apparatuses, image sensors, or the like.

The above information disclosed in this Background section is only for understanding of the background of the inventive concepts, and, therefore, it may contain information that does not constitute prior art.

SUMMARY

Applicant discovered that it is difficult for an organic photodetector of the related art to secure high external quantum efficiency and low dark current simultaneously because as a reverse bias applied to the organic photodetector increases, the response rate increases, whereas as a dark current tends to increase, noise of the organic photodetector increases.

Organic photodetectors and electronic devices including the same constructed according to illustrative principles and implementations of the invention have improved light detection efficiency. For example, Applicant discovered that when the distance between a first hole transport layer, which is inserted in the middle of a hole transport layer, and a first electrode of the optical detector satisfies the ranges disclosed herein, the organic photodetector may have improved external quantum efficiency. More specifically, organic photodetectors constructed according to the principles and embodiments of the invention may exhibit low dark current, and at the same time improved external quantum efficiency, thus providing excellent light detection characteristics.

Additional features of the inventive concepts will be set forth in the description which follows, and in part will be apparent from the description, or may be learned by practice of the inventive concepts.

According to one aspect of the invention, an organic photodetector includes: a first electrode; a second electrode facing the first electrode; an activation layer between the first electrode and the second electrode; a hole injection layer between the first electrode and the activation layer; and a hole transport layer between the hole injection layer and the activation layer, wherein the hole transport layer includes: a first hole transport layer including a p-dopant; and a second hole transport layer not including a p-dopant.

The first hole transport layer may be disposed in the middle of the second hole transport layer, and a distance between a surface of the first electrode facing the second electrode and a surface of the first hole transport layer facing the first electrode may be about 450 Å to about 1200 Å.

The distance between the surface of the first electrode facing the second electrode and the surface of the first hole transport layer facing the first electrode may be about 450 Å to about 650 Å, or about 900 Å to about 1200 Å.

The first hole transport layer may be between the hole injection layer and the second hole transport layer, and the hole injection layer and the second hole transport layer may be in direct contact with each other.

The first hole transport layer may be between the second hole transport layer and the activation layer, and the second hole transport layer and the activation layer may be in direct contact with each other.

The p-dopant may include a compound having a lowest unoccupied molecular orbital energy level of less than about −3.5 eV.

The first hole transport layer may further include a hole transport material.

The hole transport material may include a compound of Formula 202 or any combination of compounds of Formula 202:

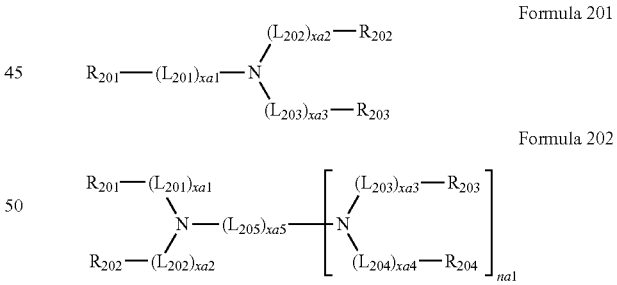

with the variables as defined herein.

The amount of the p-dopant in the first hole transport layer may be about 0.1 vol. % to about 10 vol. %.

The first hole transport layer may have a thickness of about 5 Å to about 150 Å.

The activation layer may include: a p-type semiconductor layer including a p-type organic semiconductor; and an n-type semiconductor layer including an n-type organic semiconductor, and the p-type semiconductor layer and the n-type semiconductor layer may form a PN junction.

The activation layer may include: a p-type semiconductor layer including a p-type organic semiconductor; and an n-type semiconductor layer including an n-type organic semiconductor, and a mixed layer of the p-type organic semiconductor and the n-type organic semiconductor.

The p-type organic semiconductor may include SubPc, CuPc, DBP, or any combination thereof, and the n-type organic semiconductor may include C60 fullerene, C70 fullerene, or any combination thereof.

The organic photodetector may have a dark current density of about $1 \times 10^{-4}$ mA/cm$^2$ or less when a reverse bias of $-3$V is applied.

The organic photodetector may not include an electron blocking layer between the first electrode and the activation layer.

The first electrode may include an anode, the second electrode may include a cathode, the organic photodetector may further include an electron transport region between the activation layer and the second electrode, and the electron transport region may include a hole blocking layer, an electron transport layer, an electron injection layer, or any combination thereof.

The electron transport region may include the hole blocking layer, the electron transport layer, and the electron injection layer arranged sequentially from the activation layer.

An electronic apparatus may include the organic photodetector as described above.

The electronic apparatus may further include a light-emitting device.

According to another aspect of the invention, an electronic apparatus includes: a substrate including a light detection region and a light emission region; an organic photodetector on the light detection region; and a light-emitting device on the light emission region, wherein the organic photodetector includes: a first pixel electrode; a second electrode facing the first pixel electrode; and a hole injection layer, a hole transport layer, and an activation layer arranged sequentially between the first pixel electrode and the second electrode, wherein the hole transport layer includes: a first hole transport layer including a p-dopant; and a second hole transport layer not including a p-dopant, the light-emitting device includes: a second pixel electrode; the second electrode facing the second pixel electrode; and the hole injection layer, the second hole transport layer, and an emission layer arranged sequentially between the second pixel electrode and the second electrode, the first pixel electrode, the first hole transport layer, and the activation layer at least partially overlap the light detection region, the second pixel electrode and the emission layer at least partially overlap the light emission region, and the hole injection layer, the second hole transport layer, and the counter electrode overlap substantially the entirety of the light detection region and the light emission region.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
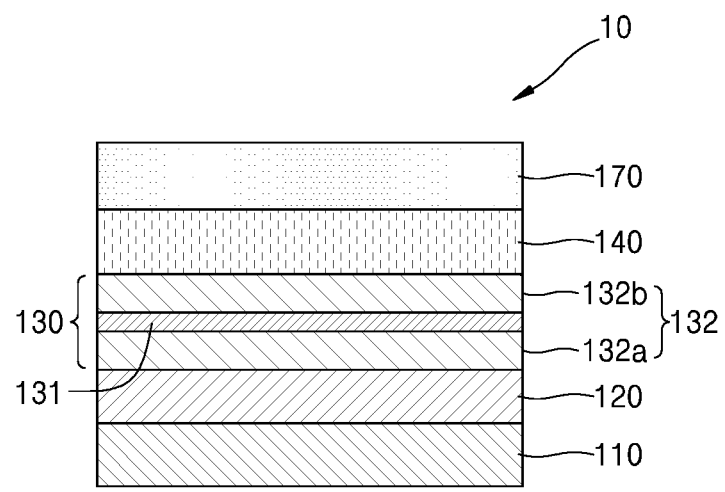
FIG. 1 is a schematic cross-sectional view of an embodiment of an organic photodetector constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements, and repetitive explanations are omitted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, processes, steps, operations, elements, components, combinations, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
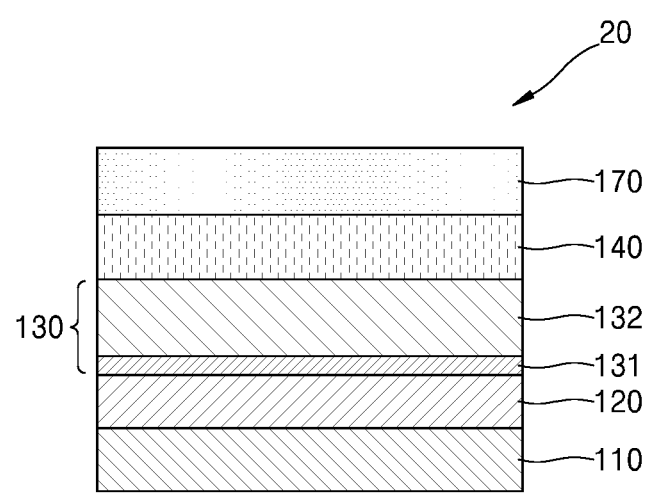
FIG. 2 is a schematic cross-sectional view of another embodiment of an organic photodetector constructed according to the principles of the invention.
Figure 3:
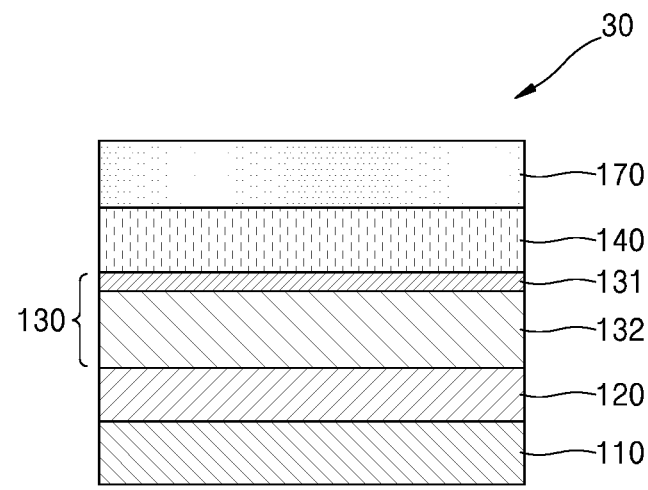
FIG. 3 is a schematic cross-sectional view of a further embodiment of an organic photodetector constructed according to the principles of the invention.

Description of FIGS. 1 to 3

FIG. 1 is a schematic cross-sectional view of an embodiment of an organic photodetector constructed according to the principles of the invention.

Referring to FIG. 1, an organic photodetector 10 includes: a first electrode 110, a second electrode 170 facing the first electrode 110, an activation layer 140 located between the first electrode 110 and the second electrode 170, a hole injection layer 120 located between the first electrode 110 and the activation layer 140, and a hole transport layer 130 located between the hole injection layer 120 and the activation layer 140. The hole transport layer 130 include a first hole transport layer 131 and a second hole transport layer 132.

One of the first electrode 110 and the second electrode 170 may be an anode, and the other one may be a cathode. For example, the first electrode 110 may be an anode, and the second electrode 170 may be a cathode.

The first hole transport layer 131 includes a p-dopant, and the second hole transport layer 132 does not include a p-dopant. That is, the first hole transport layer 131 may be a p-doped hole transport layer. The p-dopant is substantially not present in the second hole transport layer 132. That is, the second hole transport layer 132 may be an undoped hole transport layer.

Referring to FIG. 1, the first hole transport layer 131 may inserted in the middle of the hole transport layer 130. Accordingly, the second hole transport layer 132 may include one part, namely, a second hole transport layer 132a located between the hole injection layer 120 and the first hole transport layer 131, and another part, namely, a second hole transport layer 132b located between the first hole transport layer 131 and the activation layer 140. In this case, the first hole transport layer 131 may be in direct contact with each of the second hole transport layer 132a and the another second hole transport layer 132b.

The hole transport region of the organic photodetector 10 may include a structure in which the hole injection layer 120, the second hole transport layer 132a, the first hole transport layer 131, and the another part of the second hole transport layer 132b are arranged sequentially on the first electrode 110.

In one or more embodiments, the another part of the second hole transport layer 132b may be in direct contact with the activation layer 140. That is, the organic photodetector 10 may not include an electron blocking layer between the first electrode 110 and the activation layer 140.

When the first hole transport layer 131 is inserted in the middle of the hole transport layer 130, the hole transport layer 130 may have improved conductivity and may accelerate the rate of movement of holes moving in the hole transport layer 130. In addition, in comparison with a case where the hole transport layer 130 is entirely p-doped, due to having the p-doped hole transport layer inserted in the middle of the hole transport layer 130. Although not wanting to be bound by theory, the external quantum efficiency may be improved by the principle of charge acceleration due to an electric field.

In one or more embodiments, the distance between the surface of the first electrode 110 in the direction of the second electrode 170 and the surface of the first hole transport layer 131 in the direction of the first electrode 110 may be about 450 Å to about 1200 Å. For example, the distance between the surface of the first electrode 110 in the direction of the second electrode 170 and the surface of the first hole transport layer 131 in the direction of the first electrode 110 may be about 450 angstrom (Å) to about 650 Å, or about 900 Å to about 1200 Å. The total thickness of the hole transport layer including the first hole transport layer 131 and the second hole transport layer 132 may be about 1000 Å to about 2050 Å, for example, about 1250 Å to about 2050 Å, but embodiments are not limited thereto. When the distance between the first hole transport layer 131, which is inserted in the middle of the hole transport layer, and the first electrode 110 satisfies the above ranges, the organic photodetector 10 may have improved external quantum efficiency. In one or more embodiments, when the first hole transport layer 131 is inserted in the middle of the hole transport layer 130, the first hole transport layer 131 may have a thickness of about 5 Å to about 150 Å, for example, about 5 Å to about 100 Å.

FIG. 2 is a schematic cross-sectional view of another embodiment of an organic photodetector constructed according to the principles of the invention.

Particularly, FIG. 2 is a schematic cross-sectional view of another organic photodetector 20 according to an embodiment. Referring to FIG. 2, a first hole transport layer 131 may be located between a hole injection layer 120 and a second hole transport layer 132, and may be in direct contact with each of the hole injection layer 120 and the second hole transport layer 132. That is, the first hole transport layer 131 may be located at the interface between the hole injection layer 120 and the second hole transport layer 132. The hole transport region of the organic photodetector 20 may include a structure in which the hole injection layer 120, the first hole transport layer 131, and the second hole transport layer 132 are arranged sequentially on the first electrode 110.

The first hole transport layer 131 may have high conductivity, and thus efficiently transport, into the hole injection layer 120, holes delivered from the second hole transport layer 132. Accordingly, the organic photodetector 20 may have an improved quantum efficiency. In addition, in comparison with a case where the hole transport layer 130 is entirely p-doped, due to having the undoped hole transport layer and the p-doped hole transport layer as separate layers. Although not wanting to be bound by theory, external quantum efficiency may be improved by the principle of charge acceleration due to an electric field.

In one or more embodiments, the second hole transport layer 132 may be in direct contact with the activation layer 140. That is, the organic photodetector 20 may not include an electron blocking layer between the first electrode 110 and the activation layer 140. In other embodiments, the organic photodetector 20 may further include another first hole transport layer 131 between the second hole transport layer 132 and the activation layer 140. The another first hole transport layer 131 may be in direct contact with each of the second hole transport layer 132 and the activation layer 140. Accordingly, the organic photodetector 20 may include two first hole transport layers 131, and the two hole transport layers 131 may be located at the interface between the second hole transport layer 132 and the hole injection layer 120, and at the interface between the second hole transport layer 132 and the activation layer 140, respectively.

FIG. 3 is a schematic cross-sectional view of a further embodiment of an organic photodetector constructed according to the principles of the invention.

Particularly, FIG. 3 is a schematic cross-sectional view of a further organic photodetector 30 according to another embodiment. Referring to FIG. 3, a first hole transport layer 131 may be located between a second hole transport layer 132 and an activation layer 140, and may be in direct contact with each of the second hole transport layer 132 and the activation layer 140. A hole transport region of the organic photodetector 30 may include a structure in which a hole injection layer 120, the second hole transport layer 132, and the first hole transport layer 131 are arranged sequentially on the first electrode 110.

The first hole transport layer 131 can efficiently transport holes generated in the activation layer 140 to the adjacent second hole transport layer 132. Accordingly, the organic photodetector 30 may have an improved quantum efficiency. In addition, in comparison with a case where the hole transport layer 130 is entirely p-doped, due to having the undoped hole transport layer and the p-doped hole transport layer as separate layers. Although not wanting to be bound by theory, an external quantum efficiency may be improved according to the principle of charge acceleration by an electric field.

As a reverse bias applied to the organic photodetector increases, the response rate increases, whereas as a dark current tends to increase, noise of the organic photodetector increases. Accordingly, it is difficult for an organic photodetector of the related art to secure high external quantum efficiency and low dark current simultaneously. However, the organic photodetectors 10, 20, and 30 constructed according to the principles and embodiments of the invention herein include the first hole transport layer 131 as a separate layer, as described above, in the hole transport region having a double layer structure of hole injection layer/hole transport layer as in the related art, and thus may exhibit low dark current, and at the same time improved external quantum efficiency, thus having excellent light detection characteristics.

The organic photodetectors 10, 20, and 30 according to the embodiments may exhibit a dark current density of about $1 \times 10^{-4}$ milliamp per centimeter squared ($mA/cm^2$) or less with a reverse bias of −3 volt (V). That is, when a reverse bias is applied, reverse injection of charges from the electrode into the activation layer may be prevented, and thus a low dark current may be maintained with high light detection efficiency.

The p-dopant may be homogeneously or non-homogeneously dispersed in the first hole transport layer 131. The p-dopant may substantially not be present in the second hole transport layer 132. For example, a lowest unoccupied molecular orbital (LUMO) energy level of the p-dopant may be about −3.5 eV or less, for example, about −5.0 eV or less.

In one or more embodiments, the p-dopant may include a quinone derivative, a cyano group-containing compound, a compound containing element EL1 and element EL2, or any combination thereof.

Examples of the quinone derivative are tetracyanoquinodimethane (TCNQ), 2,3,5,6-tetrafluoro-7,7,8,8-tetracyanoquinodimethane (F4-TCNQ), and the like. Examples of the cyano group-containing compound are 1,4,5,8,9,11-hexaazatriphenylene-hexacarbonitrile (HAT-CN), and a compound represented by Formula 221 below. In one or more embodiments, the p-dopant may be HAT-CN, but embodiments are not limited thereto.

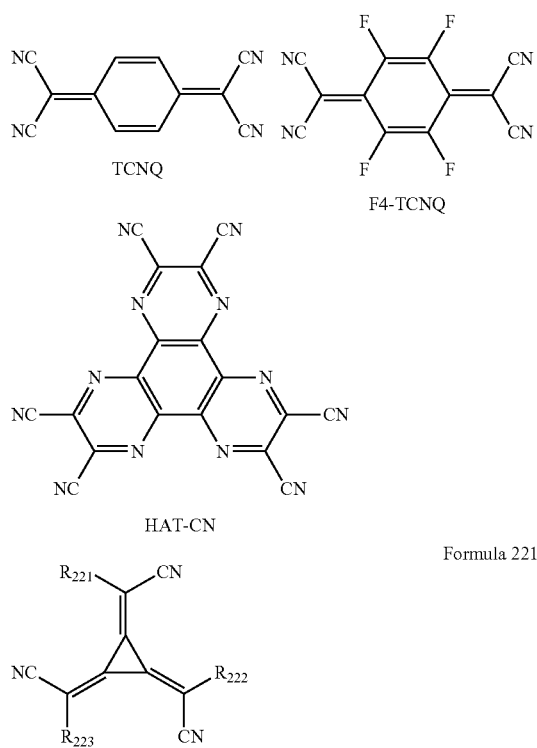

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound including element EL1 and element EL2, element EL1 may be a metal, a metalloid, or any combination thereof, and element EL2 may be a non-metal, a metalloid, or any combination thereof. Examples of the metal are an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te). Examples of the non-metal may include oxygen (O) and a halogen (for example, F, Cl, Br, I, etc.). For example, the compound containing element EL1 and element EL2 may include a metal oxide, a metal halide (for example, a metal fluoride, a metal chloride, a metal bromide, a metal iodide, or the like), a metalloid halide (for example, a metalloid fluoride, a metalloid chloride, a metalloid bromide, a metalloid iodide, or the like), a metal telluride, or any combination thereof.

Examples of the metal oxide may include a tungsten oxide (for example, WO, $W_2O_3$, $WO_2$, $WO_3$, $W_2O_5$, or the like), a vanadium oxide (for example, VO, $V_2O_3$, $VO_2$, $V_2O_5$, or the like), a molybdenum oxide (MoO, $Mo_2O_3$, $MoO_2$, $MoO_3$, $Mo_2O_5$, or the like), and a rhenium oxide (for example, $ReO_3$, or the like). Examples of the metal halide may include an alkali metal halide, an alkaline earth metal halide, a transition metal halide, a post-transition metal halide, and a lanthanide metal halide. Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI. Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhI_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), and a gold halide (for example, AuF, AuCl, AuBr, AuI, etc.).

Examples of the post-transition metal halide may include a zinc halide (for example, $ZnF_2$, $ZnCl_2$, $ZnBr_2$, $ZnI_2$, etc.), an indium halide (for example, $InI_3$, etc.), and a tin halide (for example, $SnI_2$, etc.). Examples of the lanthanide metal halide may include YbF, $YbF_2$, $YbF_3$, $SmF_3$, YbCl, $YbCl_2$, YbCl$_3$, SmCl$_3$, YbBr, YbBr$_2$, YbBr$_3$, SmBr$_3$, YbI, YbI$_2$, YbI$_3$, and SmI$_3$. Examples of the metalloid halide may include an antimony halide (for example, SbCl$_5$, etc.).

Examples of the metal telluride may include an alkali metal telluride (for example, Li$_2$Te, Na$_2$Te, K$_2$Te, Rb$_2$Te, Cs$_2$Te, etc.), an alkaline earth metal telluride (for example, BeTe, MgTe, CaTe, SrTe, BaTe, etc.), a transition metal telluride (for example, TiTe$_2$, ZrTe$_2$, HfTe$_2$, V$_2$Te$_3$, Nb$_2$Te$_3$, Ta$_2$Te$_3$, Cr$_2$Te$_3$, Mo$_2$Te$_3$, W$_2$Te$_3$, MnTe, TcTe, ReTe, FeTe, RuTe, OsTe, CoTe, RhTe, IrTe, NiTe, PdTe, PtTe, Cu$_2$Te, CuTe, Ag$_2$Te, AgTe, Au$_2$Te, etc.), a post-transition metal telluride (for example, ZnTe, etc.), and a lanthanide metal telluride (for example, LaTe, CeTe, PrTe, NdTe, PmTe, EuTe, GdTe, TbTe, DyTe, HoTe, ErTe, TmTe, YbTe, LuTe, etc.).

In one or more embodiments, the first hole transport layer 131 may further include, in addition to the p-dopant, a hole transport material. In this case, the first hole transport layer 131 may be formed by doping a hole transport material with the p-dopant. In one or more embodiments, the second hole transport layer 131 may include a hole transport material. The hole transport material included in the first hole transport layer 131 and the hole transport material included in the second hole transport layer 132 may be identical to each other.

In one or more embodiments, the amount of the p-dopant in the first hole transport layer 131 may be about 0.1 volume percent (vol. %) to about 10 vol. %, for example, about 0.5 vol. % to about 5 vol. %. When the amount of the p-dopant satisfies the above ranges, a low dark current may be maintained, and at the same time external quantum efficiency may be improved. In one or more embodiments, the first hole transport layer 131 may have a thickness of about 5 Å to about 150 Å, for example about 10 Å to about 100 Å, or about 50 Å to about 100 Å.

The activation layer 140 generates excitons in response to light irradiation from the outside and divides the generated excitons into holes and electrons. The activation layer 140 may include a p-type organic semiconductor and an n-type organic semiconductor. In one or more embodiments, the activation layer 140 may include a p-type semiconductor layer including the p-type organic semiconductor, and an n-type semiconductor layer including the n-type organic semiconductor, and the p-type semiconductor layer and the n-type semiconductor layer may form a PN junction.

Although not wanting to be bound by theory, because the p-type organic semiconductor acts as an electron donor, and the n-type organic semiconductor acts as an electron acceptor, excitons can be efficiently divided into holes and electrons by photo-induced charge separation occurring at the interface between the p-type semiconductor layer and the n-type semiconductor layer. In addition, because the activation layer 140 is divided into the p-type semiconductor layer and the n-type semiconductor layer, capture and migration of holes and electrons generated at the interface may be facilitated.

In one or more embodiments, the activation layer 140 may be a mixed layer in which the p-type organic semiconductor and the n-type organic semiconductor are mixed. In this case, the activation layer 140 may be formed by co-deposition of the p-type organic semiconductor and the n-type organic semiconductor. When the activation layer 140 is the mixed layer, excitons can be generated with a diffusion distance from the donor-acceptor interface, and thus, the organic photodetector may have improved external quantum efficiency.

In one or more embodiments, the p-type organic semiconductor may be a compound that serves as an electron donor supplying electrons. For example, the p-type organic semiconductor may include boron subphthalocyanine chloride (SubPc), copper(II)phthalocyanine (CuPc), tetraphenyldibenzo periflanthene (DBP), or any combination thereof, but embodiments are not limited thereto.

In one or more embodiments, the n-type organic semiconductor may be a compound that serves as an electron acceptor accepting electrons. For example, the n-type organic semiconductor may include a (C60-Ih)[5,6]fullerene (C60 fullerene), a (C70-D5h(6))[5,6]fullerene (C70 fullerene), or any combination thereof, but embodiments are not limited thereto. The activation layer 140 may have a thickness of about 200 Å to about 2000 Å, for example, about 400 Å to about 600 Å.

First Electrode 110

A substrate may be additionally located under the first electrode 110 or on the second electrode 170 of FIGS. 1 to 3. As the substrate, a glass substrate or a plastic substrate may be used. In one or more embodiments, the substrate may be a flexible substrate, and may include plastics with excellent heat resistance and durability, such as a polyimide, a polyethylene terephthalate (PET), a polycarbonate, a polyethylene naphthalate, a polyarylate (PAR), a polyetherimide, or any combination thereof.

The first electrode 110 may be formed by, for example, depositing or sputtering a material for forming the first electrode 110 on the substrate. When the first electrode 110 is an anode, the material for forming the first electrode 110 may be a high-work function material.

The first electrode 110 may be a reflective electrode, a semi-transmissive electrode, or a transmissive electrode. To form the first electrode 110 as a transmissive electrode, an indium tin oxide (ITO), an indium zinc oxide (IZO), a tin oxide (SnO$_2$), a zinc oxide (ZnO), or any combinations thereof may be used as the material for forming the first electrode 110. In other embodiments, to form the first electrode 110 as a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as the material for forming the first electrode 110.

The first electrode 110 may have a single-layered structure consisting of a single layer, or a multi-layered structure including a plurality of layers. For example, the first electrode 110 may have a three-layered structure of an ITO/Ag/ITO.

Charge Auxiliary Layer

Embodiments of the organic photodetectors 10, 20, and 30 may include a charge auxiliary layer that facilitates migration of holes and electrons divided in the activation layer 140. The charge auxiliary layer may include a hole injection layer 120 and hole transport layers 130 and 140, which facilitate migration of holes, and an electron transport layer and an electron injection layer, which facilitates migration of electrons.

Hole Transport Region

The charge auxiliary layers located between the first electrode 110 and the activation layer 140 may be collectively referred to as a hole transport region. The hole transport region may further include an electron blocking layer, in addition to the hole injection layer 120, the first hole transport layer 131, and the second hole transport layer 132 as described above. The hole transport region may include a hole transport material. For example, the hole transport material may include a compound represented by Formula 201, a compound represented by Formula 202, or any combination thereof:

Formula 201

$$R_{201}-(L_{201})_{xa1}-N\begin{matrix}(L_{202})_{xa2}-R_{202}\\ \\ (L_{203})_{xa3}-R_{203}\end{matrix}$$

Formula 202

$$R_{201}-(L_{201})_{xa1}\diagdown\atop R_{202}-(L_{202})_{xa2}\diagup N-(L_{205})_{xa5}-\left[N\diagup(L_{203})_{xa3}-R_{203}\atop\diagdown(L_{204})_{xa4}-R_{204}\right]_{na1}$$

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16 below), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In one or more embodiments, Formulae 201 and 202 may each include at least one of groups represented by Formulae CY201 to CY217.

-continued

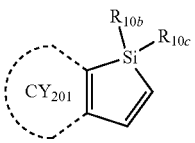

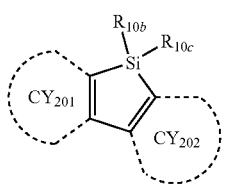

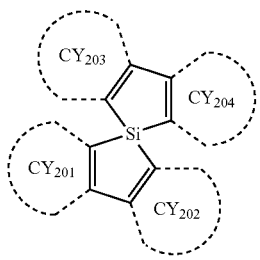

CY212

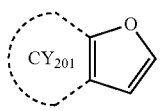

CY213

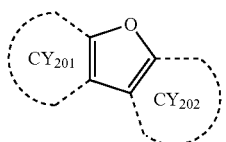

CY214

CY215

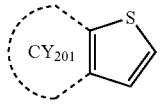

CY216

-continued

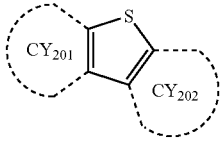

CY209

CY210

CY211

CY217

In Formulae CY201 to CY217, $R_{10b}$ and $R_{10c}$ are each the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$ as described herein. In one or more embodiments, ring CY201 to ring CY204 in Formulae CY201 to CY217 may each independently be a benzene group, a naphthalene group, a phenanthrene group, or an anthracene group.

In one or more embodiments, Formulae 201 and 202 may each include at least one of groups represented by Formulae CY201 to CY203. In one or more embodiments, Formula 201 may include at least one of groups represented by Formulae CY201 to CY203 and at least one of groups represented by Formulae CY204 to CY217.

In one or more embodiments, xa1 in Formula 201 may be 1, $R_{201}$ may be a group represented by one of Formulae CY201 to CY203, xa2 may be 0, and $R_{202}$ may be a group represented by one of Formulae CY204 to CY207. In one or more embodiments, Formulae 201 and 202 may each not include groups represented by Formulae CY201 to CY203. In one or more embodiments, Formulae 201 and 202 may each not include the groups represented by Formulae CY201 to CY203, and may include at least one of groups represented by Formulae CY204 to CY217. In one or more embodiments, Formulae 201 and 202 may each not include the groups represented by Formulae CY201 to CY217.

For example, the hole transport material may include one of Compounds HT1 to HT46, 4,4',4"-tris[phenyl(m-tolyl) amino]triphenylamine (m-MTDATA), 1-N,1-N-bis[4-(diphenylamino)phenyl]-4-N,4-N-diphenylbenzene-1,4-diamine (TDATA), 4,4',4"-tris[2-naphthyl(phenyl)amino] triphenylamine (2-TNATA), bis(naphthalen-1-yl)-N,N'-bis (phenyl)benzidine (NPB or NPD), N4,N4'-di(naphthalen-2-yl)-N4,N4'-diphenyl-[1,1'-biphenyl]-4,4'-diamine (β-NPB), N,N'-bis(3-methylphenyl)-N,N'-diphenylbenzidine (TPD), N,N'-bis(3-methylphenyl)-N,N'-diphenyl-9,9-spirobifluorene-2,7-diamine (Spiro-TPD), N2,N7-di-1-naphthalenyl-N2,N7-diphenyl-9,9'-spirobi[9H-fluorene]-2,7-diamine (Spiro-NPB), N,N'-di(1-naphthyl)-N,N-diphenyl-2,2'-dimethyl-(1,1'-biphenyl)-4,4'-diamine (methylated-NPB), 4,4'-cyclohexylidenebis[N,N-bis(4-methylphenyl)benzenamine] (TAPC), N,N,N,N'-tetrakis(3-methylphenyl)-3,3'-dimethylbenzidine (HMTPD), 4,4',4"-tris(N-carbazolyl)triphenylamine (TCTA), polyaniline/dodecylbenzenesulfonic acid (PANT/DB SA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/P S S), or any combination thereof:

HT1
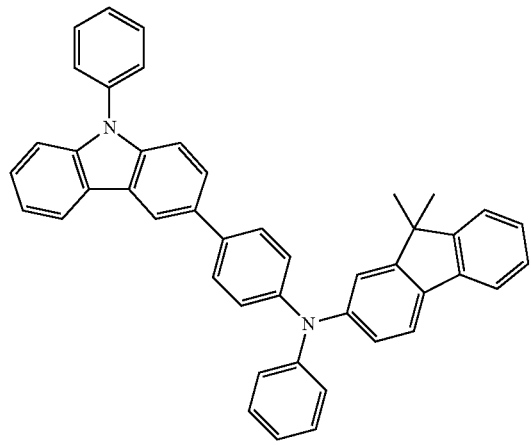
HT2
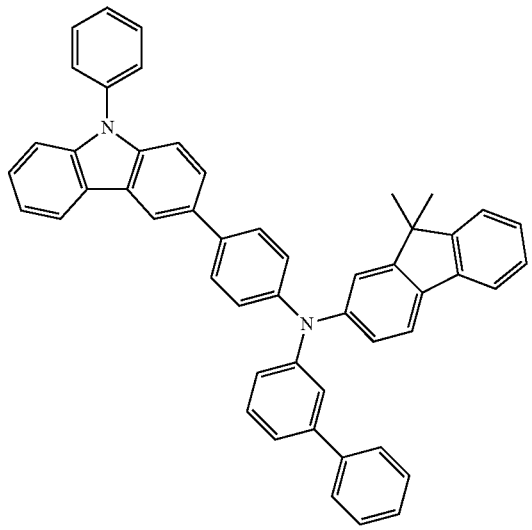
HT3
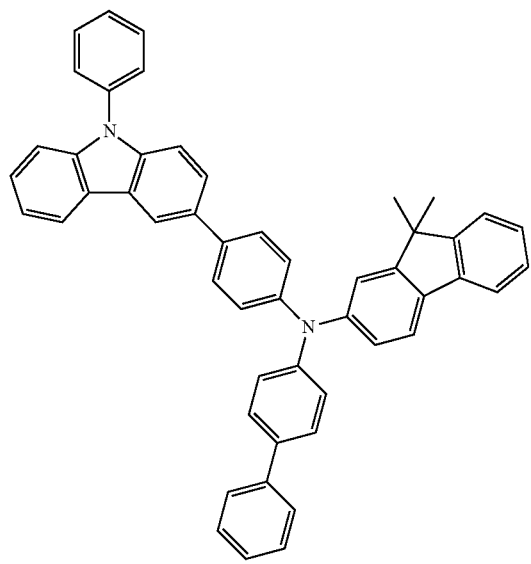
HT4
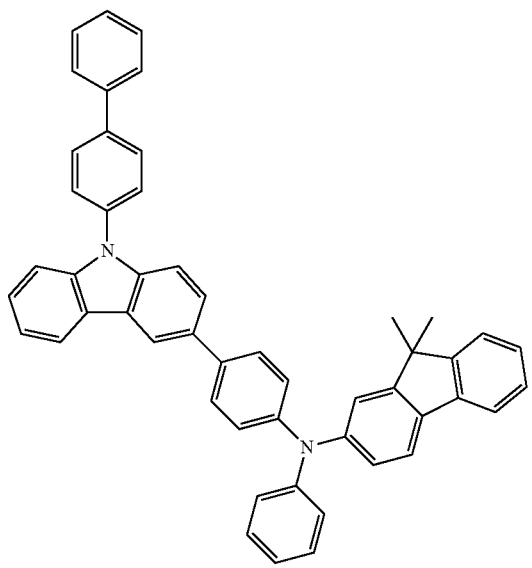

HT5
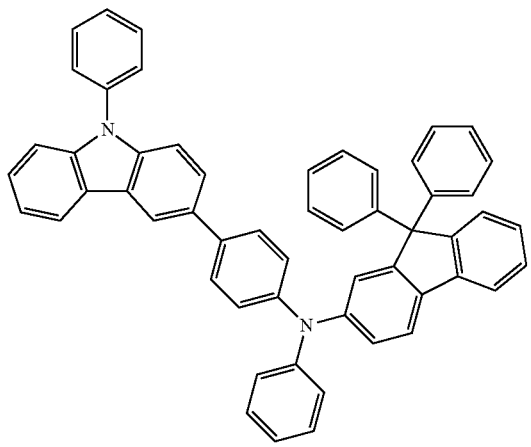
HT6
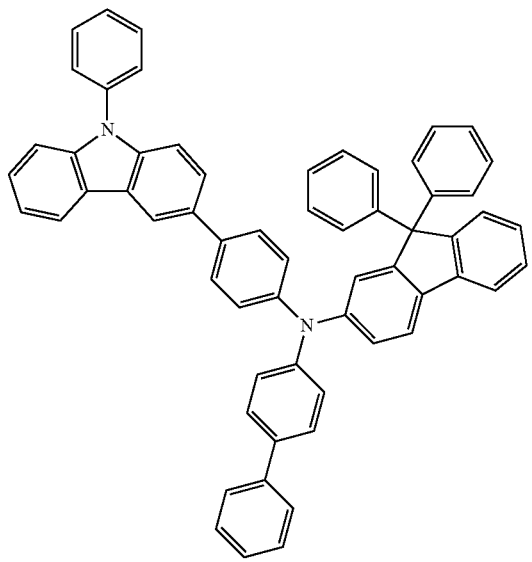
HT7
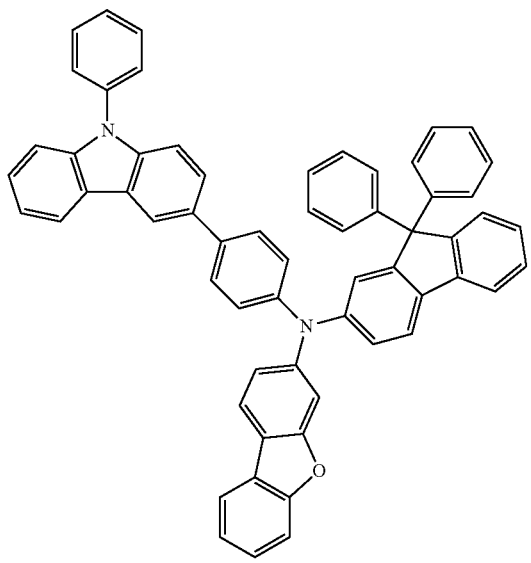
HT8
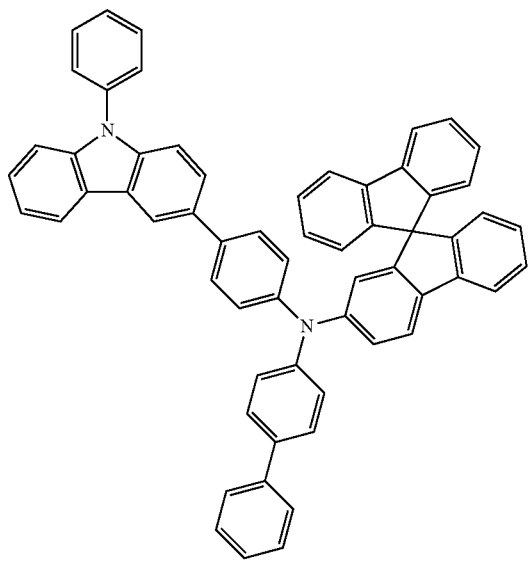

-continued
HT9
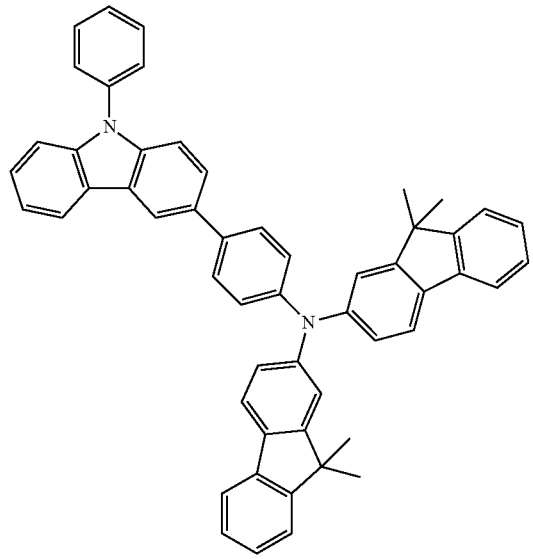
HT10
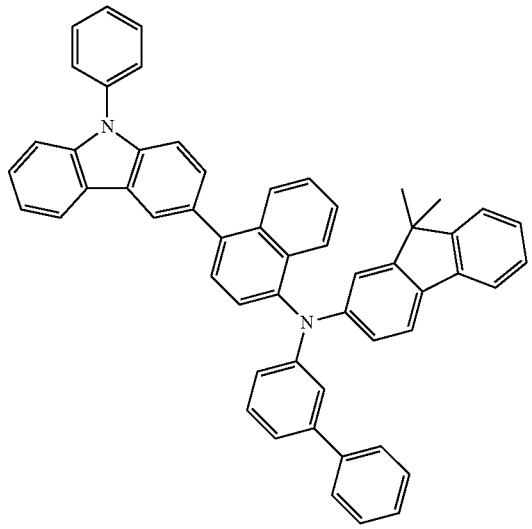
HT11
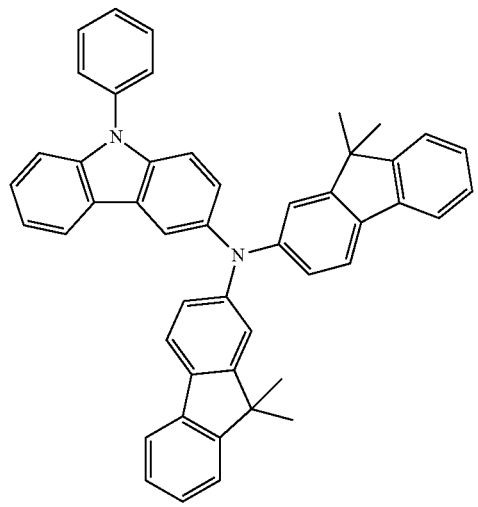
HT12
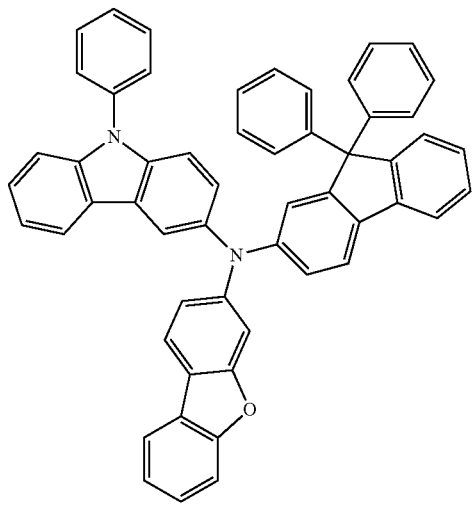
HT13
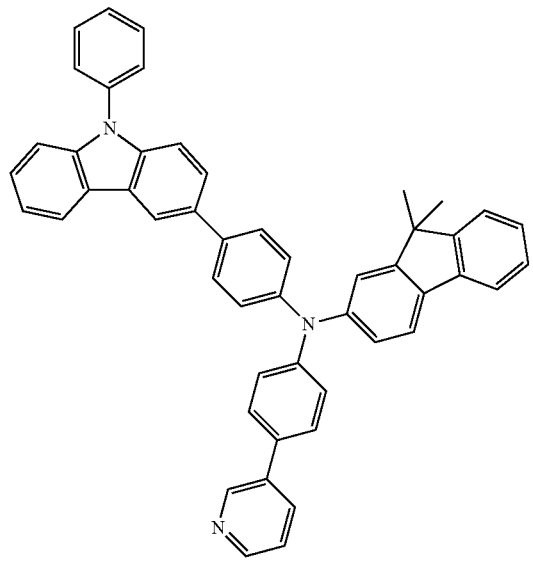
HT14
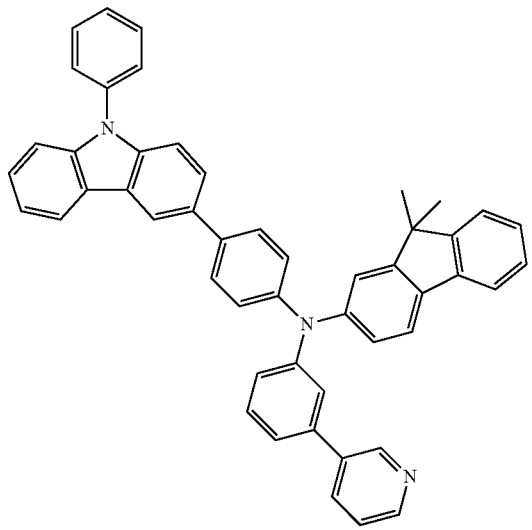

-continued
HT15
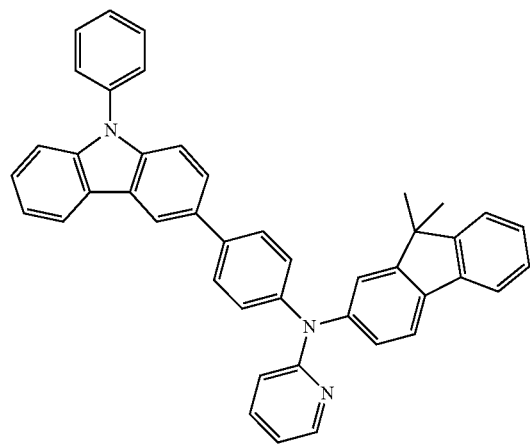
HT16
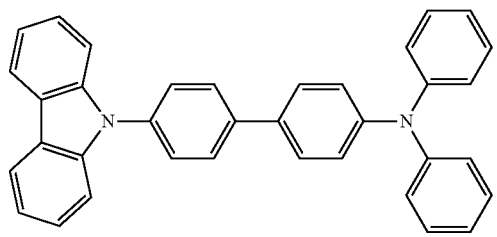
HT17
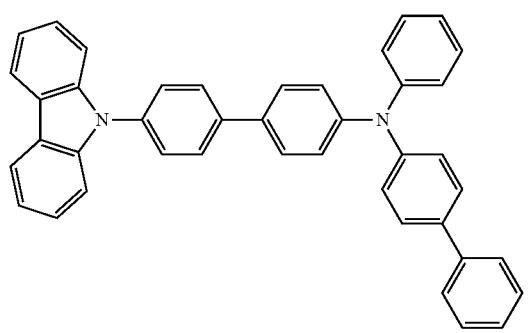
HT18
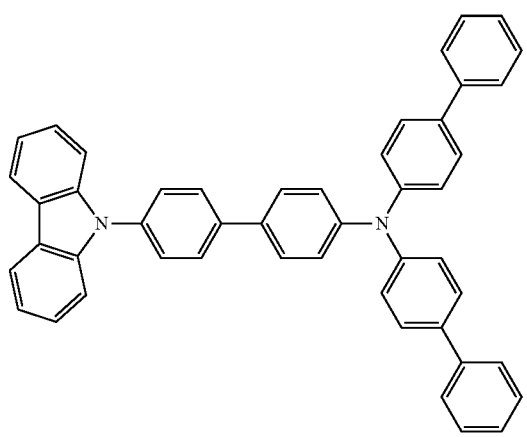
HT19
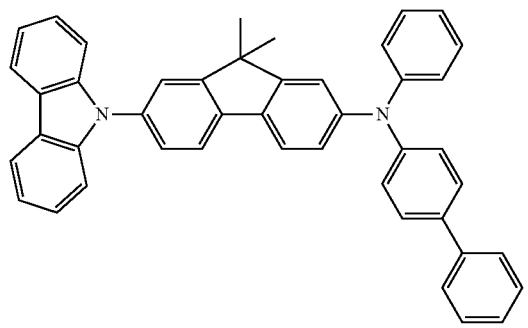
HT20
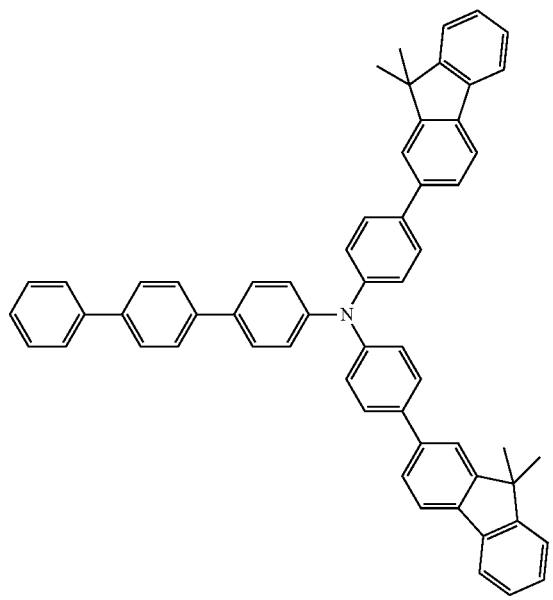

-continued
HT21
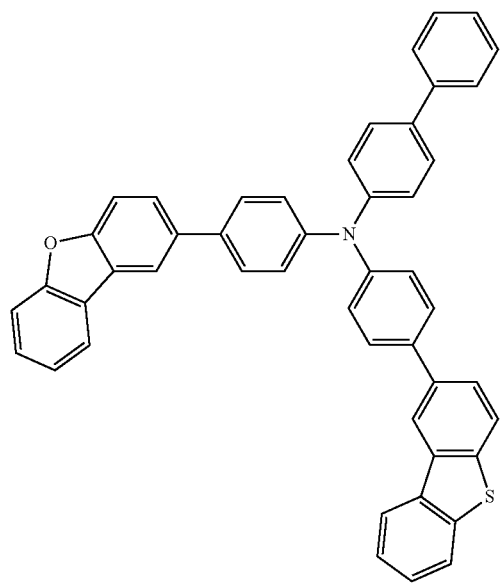
HT22
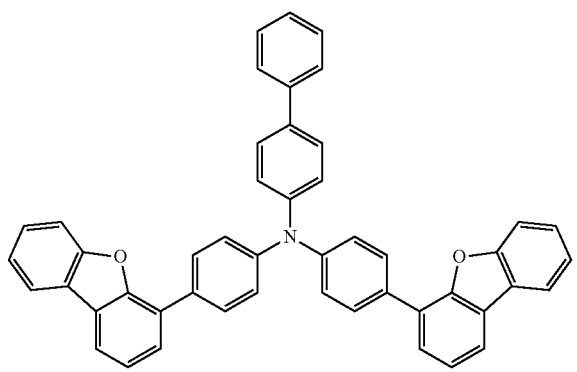
HT23
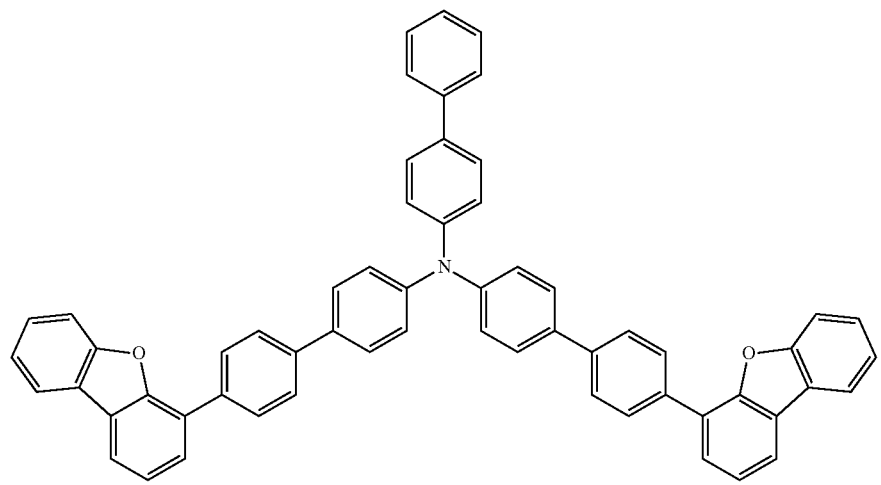
HT24
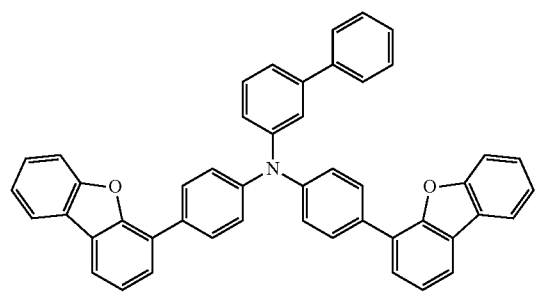
HT25
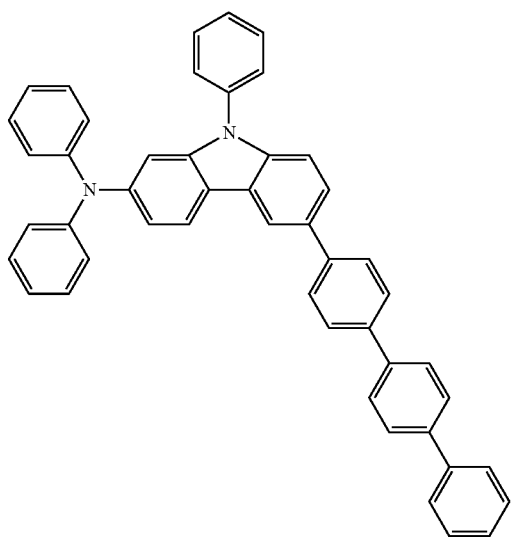

-continued
HT26
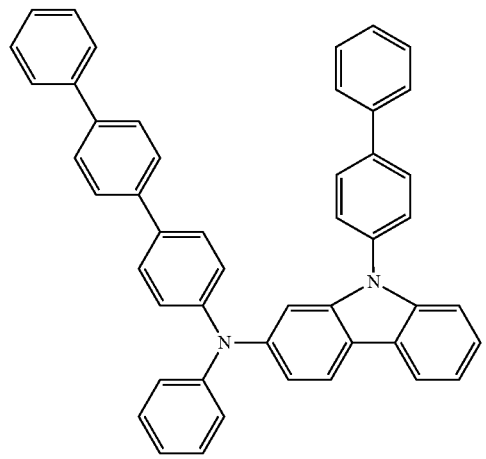
HT27
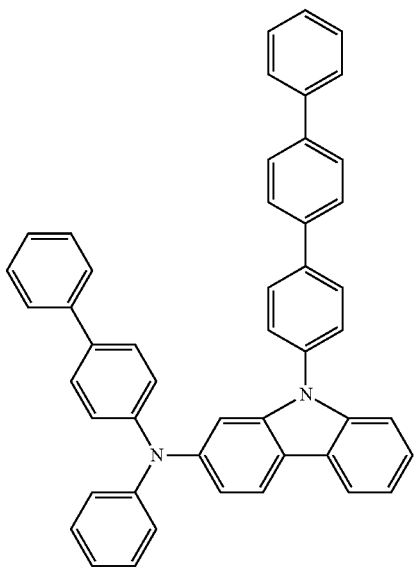
HT28
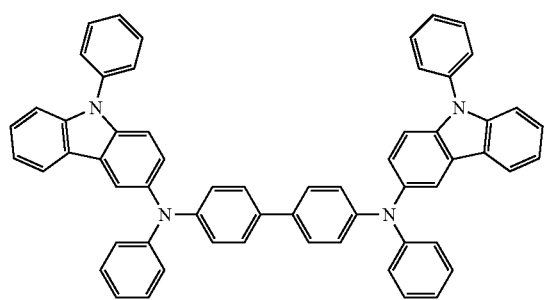
HT29
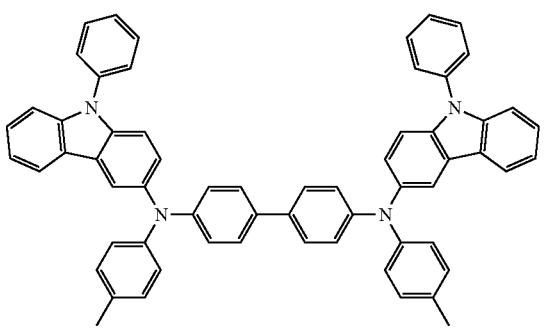
HT30
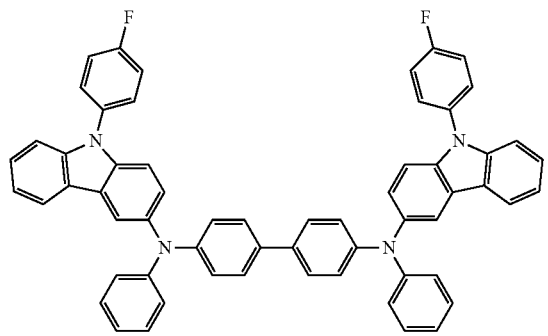
HT31
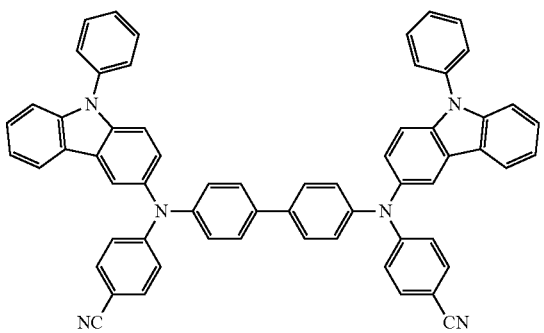

-continued
HT32
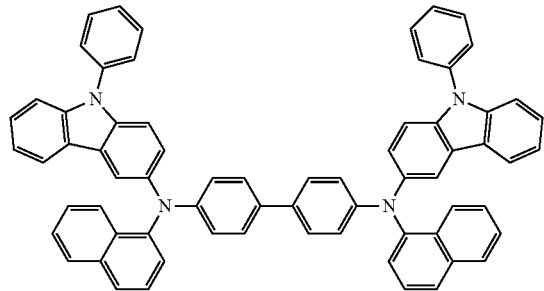
HT33
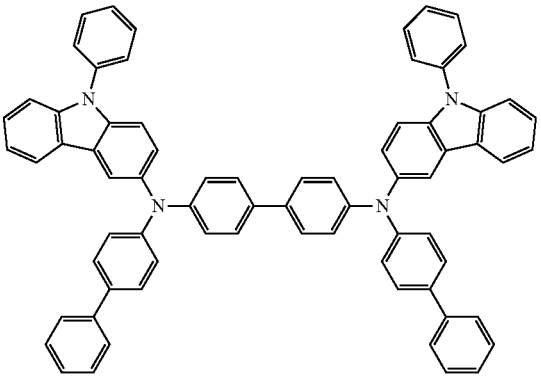
HT34
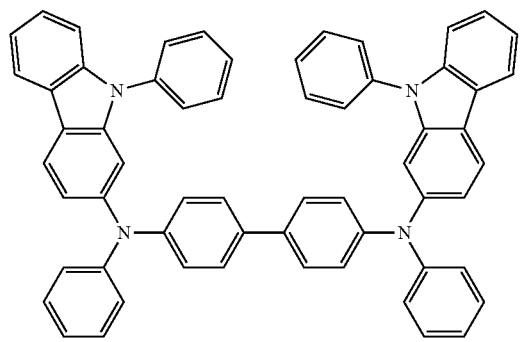
HT35
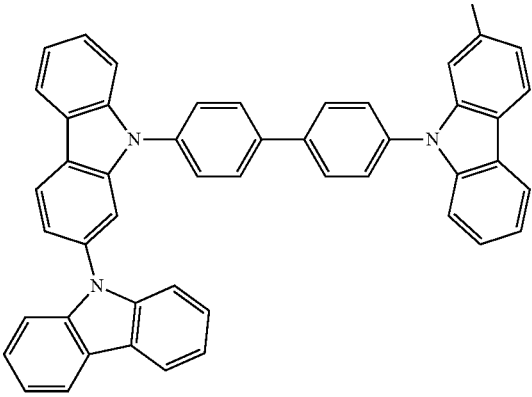
HT36
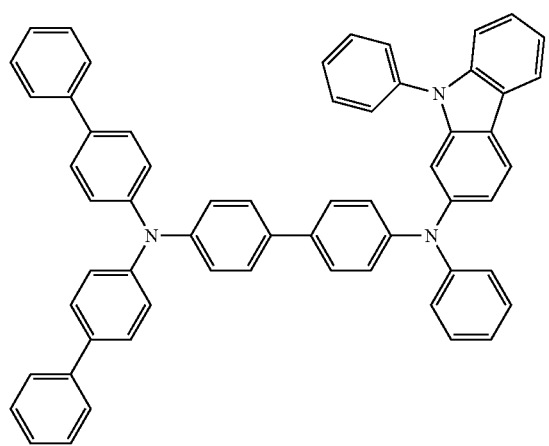
HT37
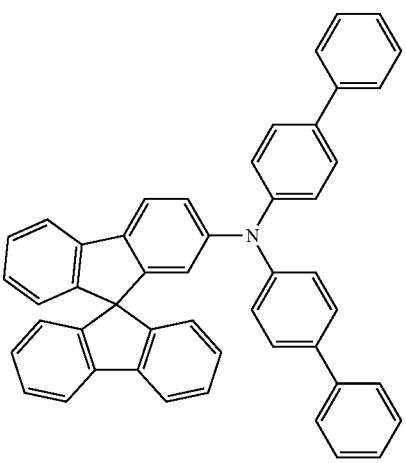

-continued
HT38
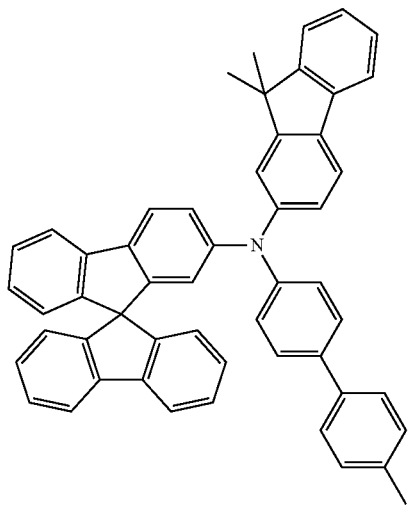
HT39
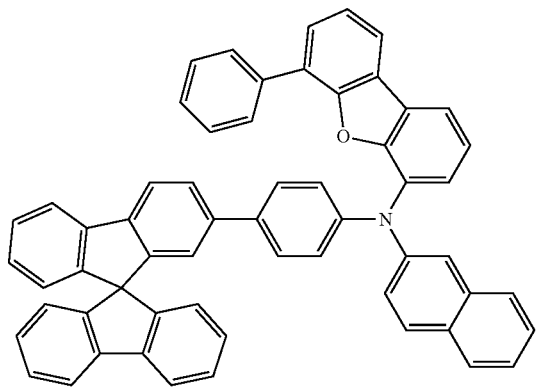
HT40
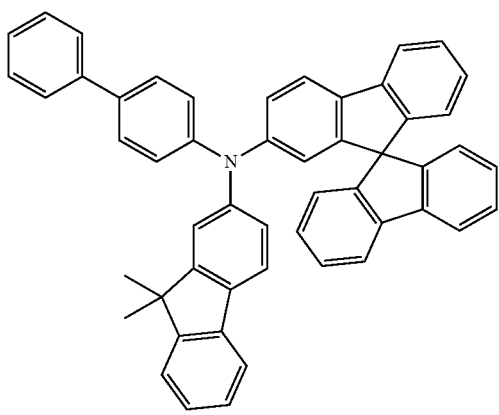
HT41
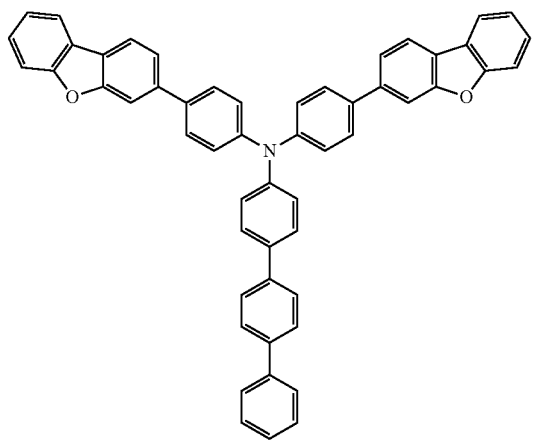
HT42
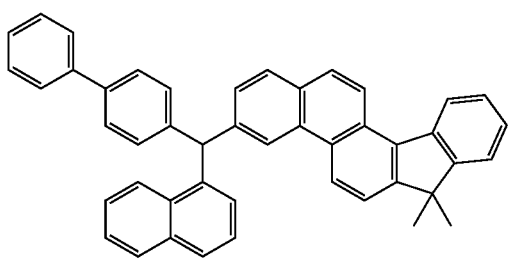
HT43
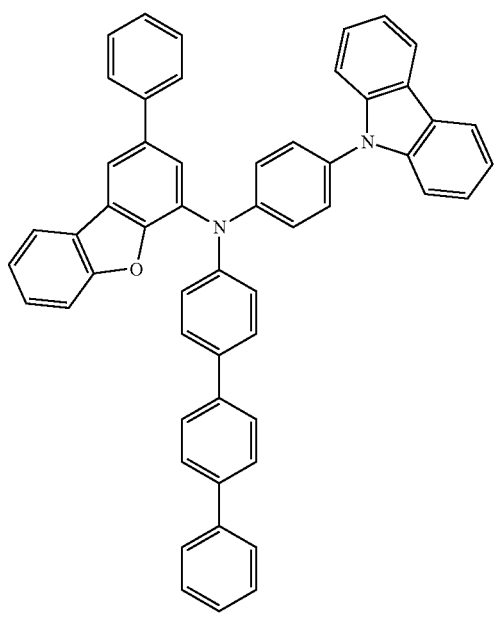

-continued
HT44
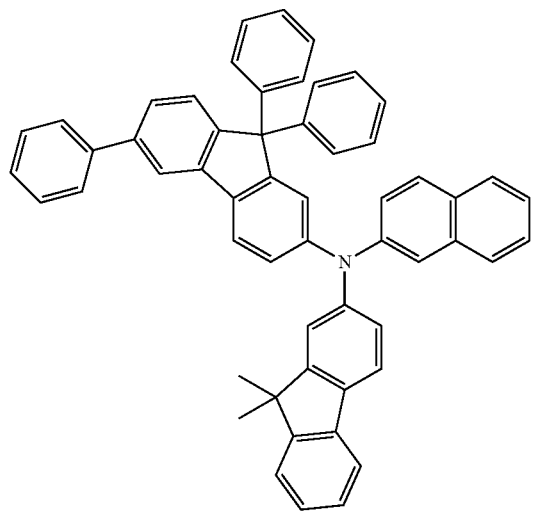
HT45
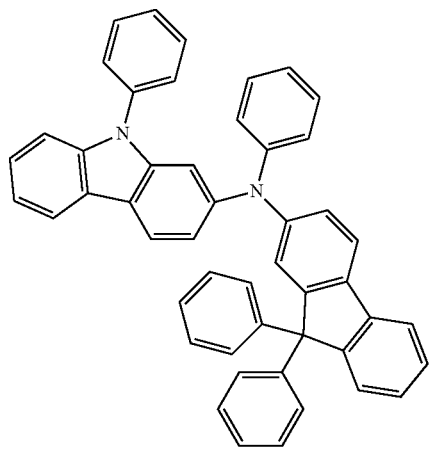
HT46
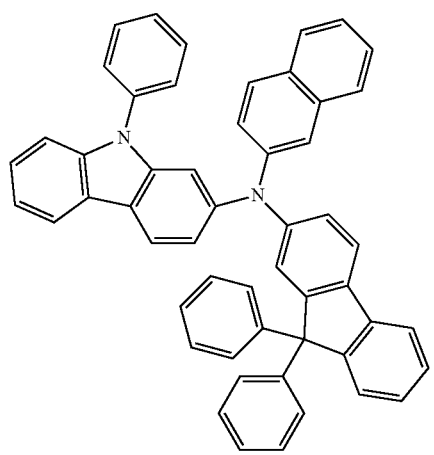
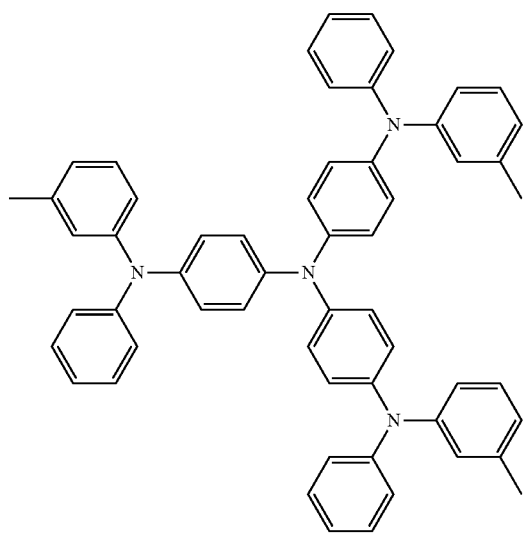
m-MTDATA

-continued
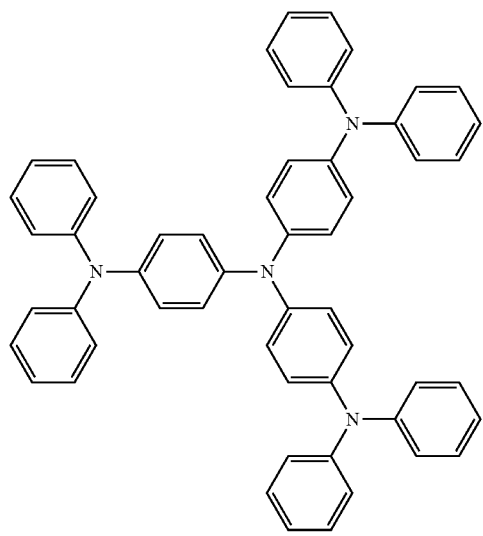
TDATA
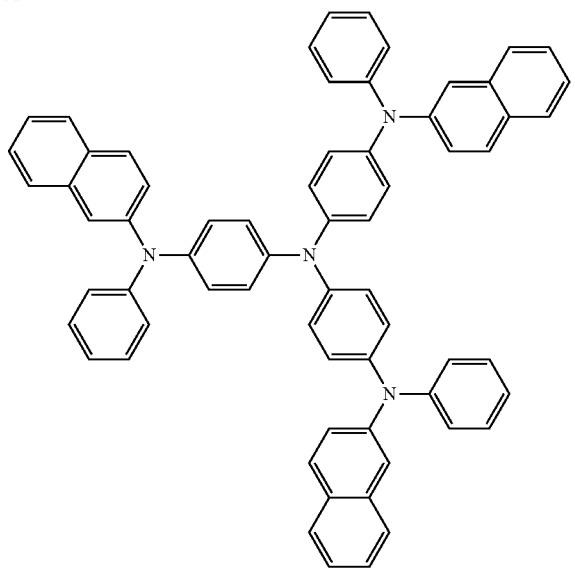
2-TNATA
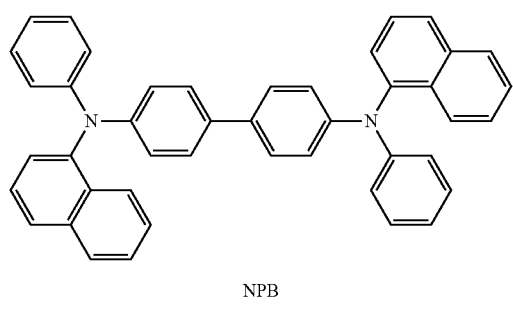
NPB
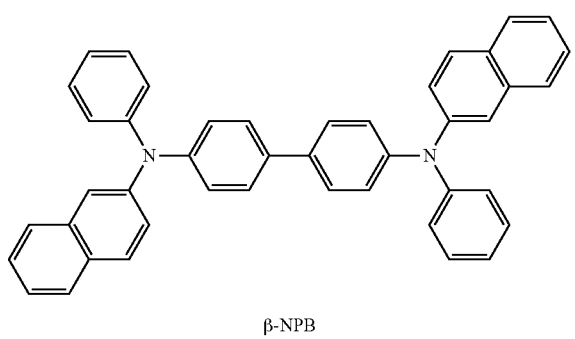
β-NPB
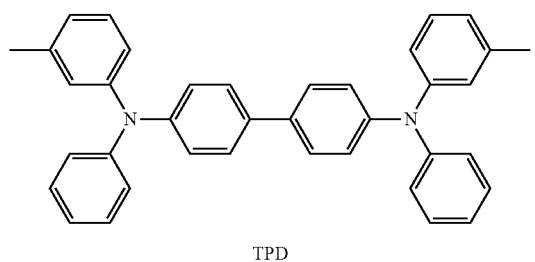
TPD
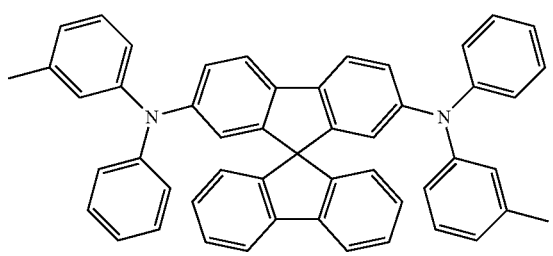
Spiro-TPD
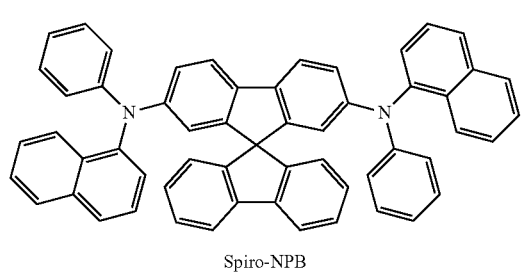
Spiro-NPB
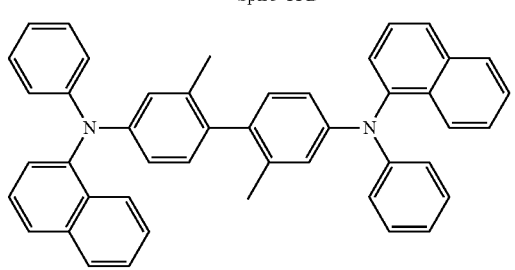
methylated-NPB

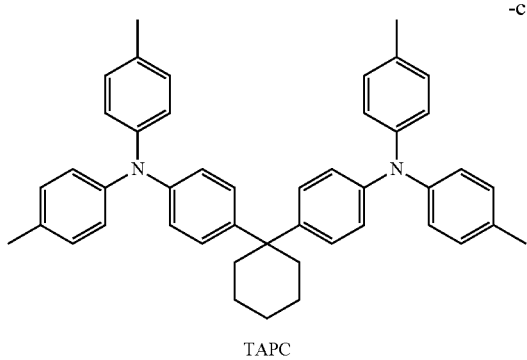

TAPC

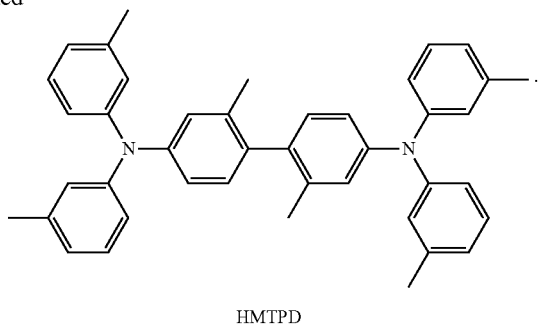

HMTPD

The thickness of the hole transport region may be in a range of about 50 Å to about 10,000 Å, for example, about 100 Å to about 4,000 Å. The thickness of the hole injection layer 120 of the hole transport region may be from about 100 Å to about 9000 Å, for example, from about 100 Å to about 1000 Å. The total thickness of the hole transport layer including the first hole transport layer 131 and the second hole transport layer 132 is from about 1000 Å to about 2050 Å, for example, from about 1250 Å to about 2050 Å, or, for example, from about 100 Å to about 1500 Å. When the thicknesses of the hole transport region, the hole injection layer 120, and the hole transport layer are within the ranges described above, satisfactory hole transport characteristics may be obtained without a substantial increase in driving voltage. The electron blocking layer serves to prevent leakage of electrons from the activation layer 140 into the hole transport region. The hole transport material as described above may be included in the electron blocking layer.

Electron Transport Region

The charge auxiliary layers located between the activation layer 140 and the second electrode 170 may be collectively referred to as an electron transport region. The electron transport region may have: i) a single-layered structure consisting of a single layer consisting of a single material, ii) a single-layered structure consisting of a single layer consisting of a plurality of different materials, or iii) a multi-layered structure including a plurality of layers including different materials.

The electron transport region may include a buffer layer, a hole blocking layer, an electron transport layer, an electron injection layer, or any combination thereof. For example, the electron transport region may have an electron transport layer/electron injection layer structure, a hole blocking layer/electron transport layer/electron injection layer structure, or a buffer layer/electron transport layer/electron injection layer structure, wherein the constituent layers of each structure are stacked sequentially from the emission layer. The electron transport region (for example, the buffer layer, the hole blocking layer, or the electron transport layer in the electron transport region) may include a metal-free compound including at least one π electron-deficient nitrogen-containing $C_1$-$C_{60}$ cyclic group.

For example, the electron transport region may include a compound represented by Formula 601 below:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ are each the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of $Ar_{601}$(s) may be linked to each other via a single bond. In one or more embodiments, $Ar_{601}$ in Formula 601 may be a substituted or unsubstituted anthracene group. In other embodiments, the electron transport region may include a compound represented by Formula 601-1:

Formula 601-1

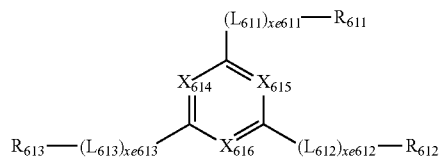

wherein, in Formula 601-1, $X_{614}$ may be N or C($R_{614}$), $X_{615}$ may be N or C($R_{615}$), $X_{616}$ may be N or C($R_{616}$), and at least one of $X_{614}$ to $X_{616}$ may be N, $L_{611}$ to $L_{613}$ are each the same as described in connection with $L_{601}$, xe611 to xe613 are each the same as described in connection with xe1, $R_{611}$ to $R_{613}$ are each the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$. For example, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), tris-(8-hydroxyquinoline)aluminum (Alq$_3$), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), 4-(naphthalen-1-yl)-3,5-diphenyl-4H-1,2,4-triazole (NTAZ), or any combination thereof:

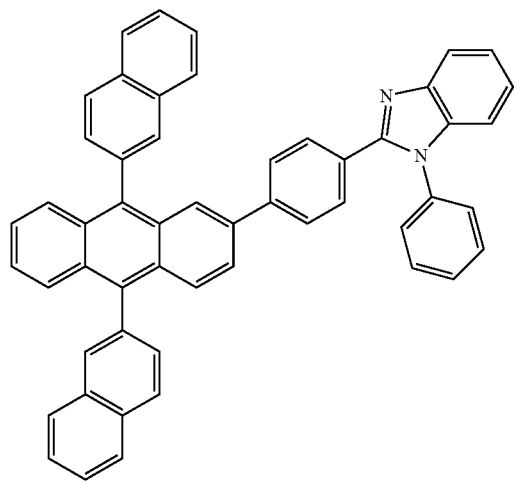

ET1

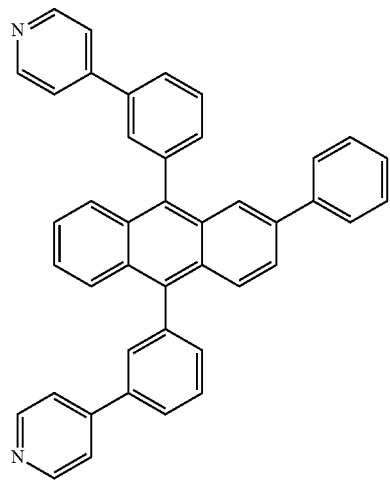

ET3

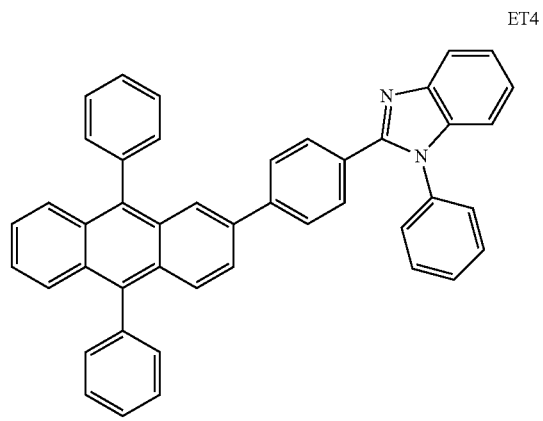

ET4

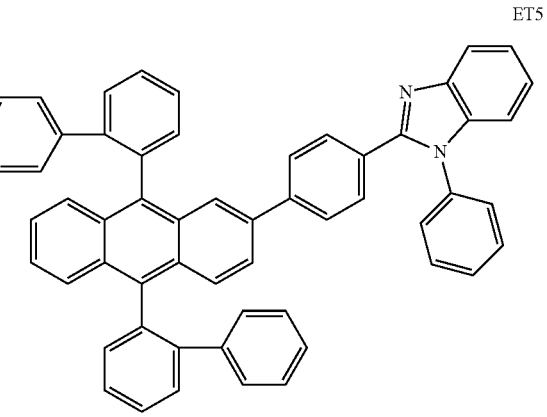

ET5

ET6
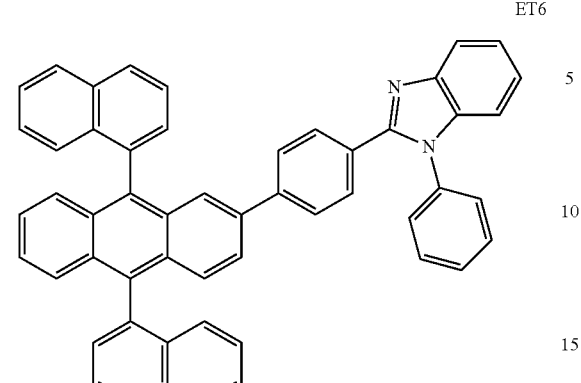
ET7
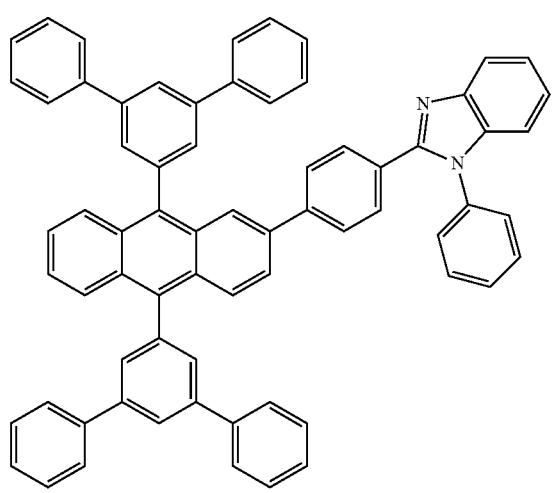
ET8
ET9
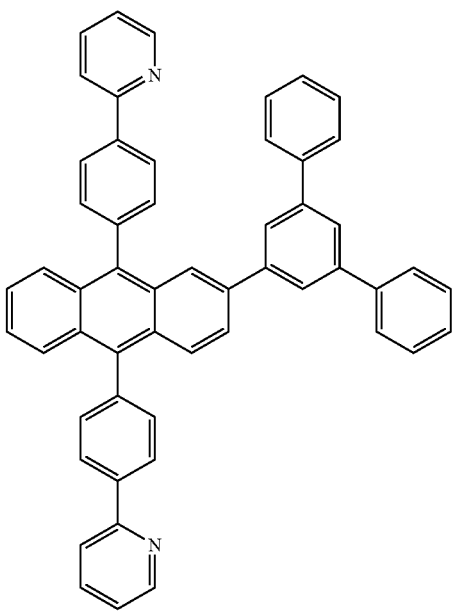
ET10
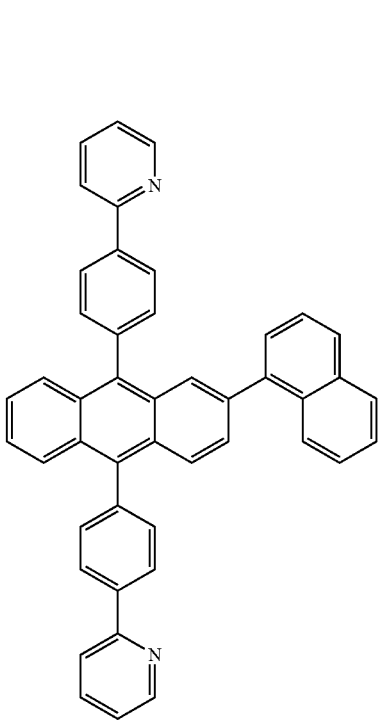

ET11
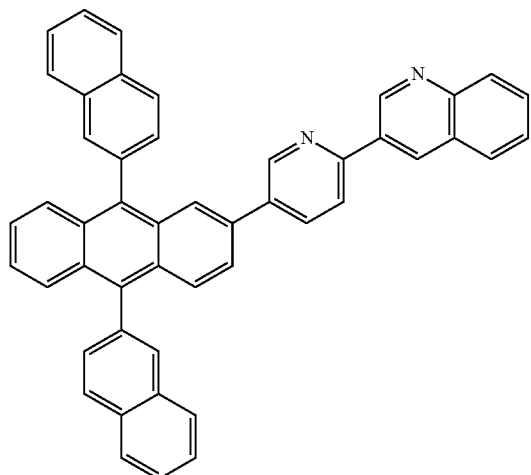
ET12
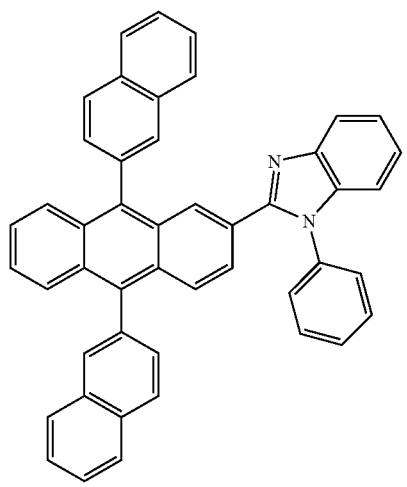
ET13
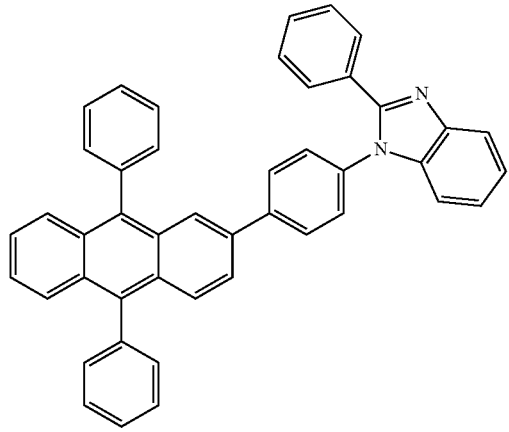
ET14
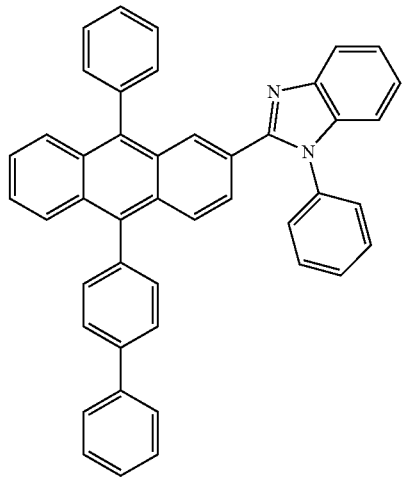
ET15
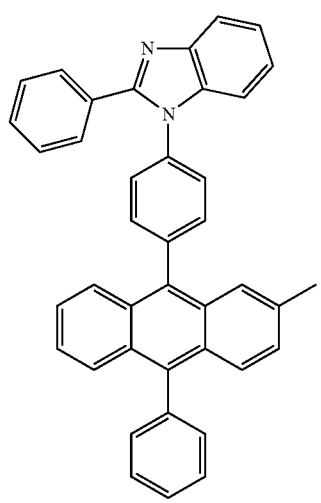
ET16
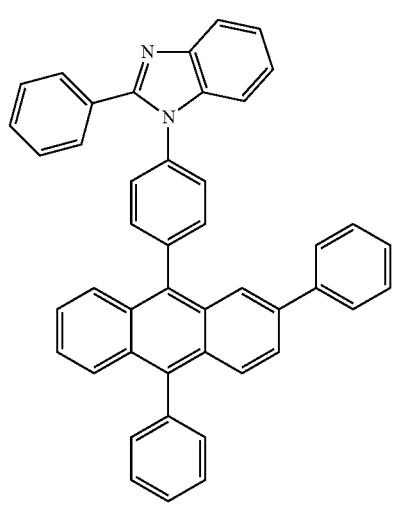

ET17
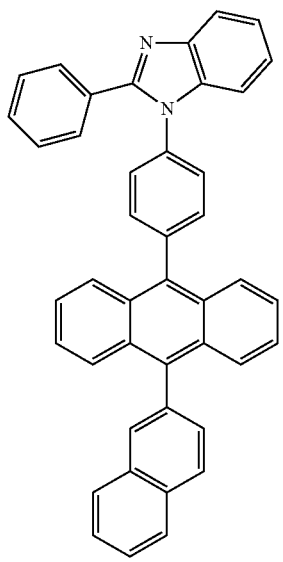
ET18
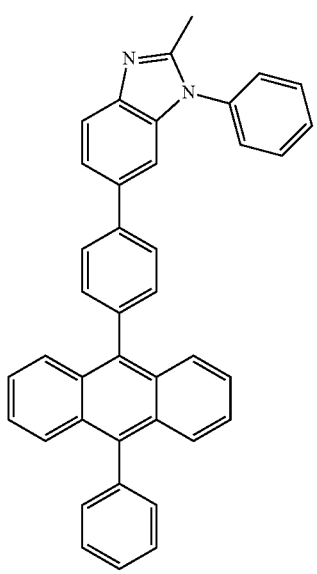
ET19
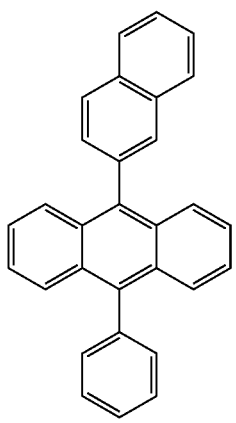
ET20
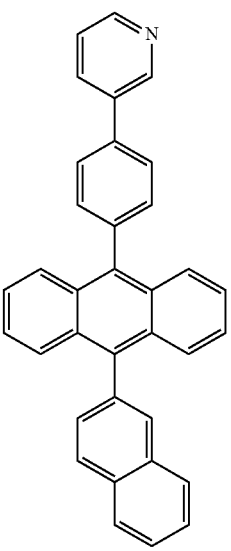
ET21
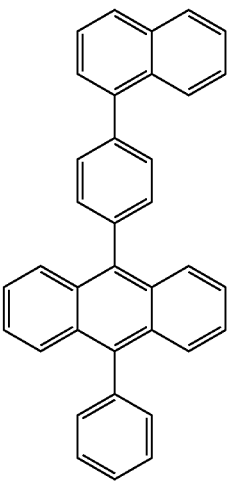
ET22
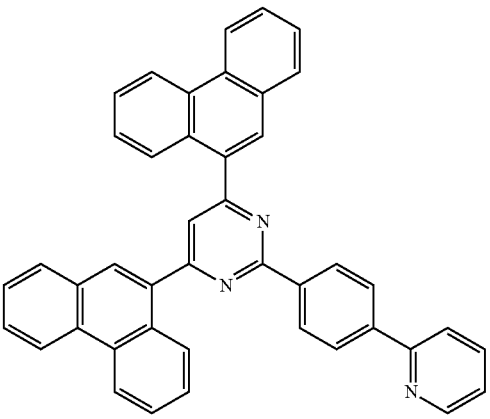

ET23
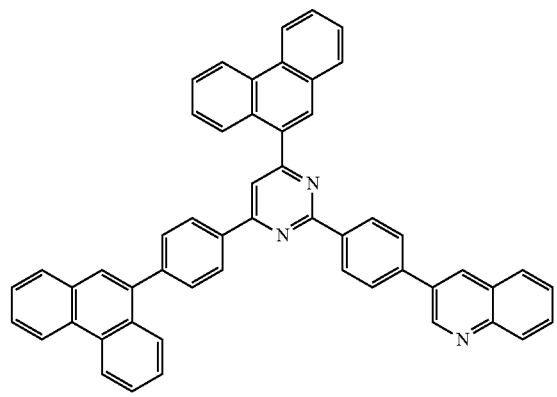
ET24
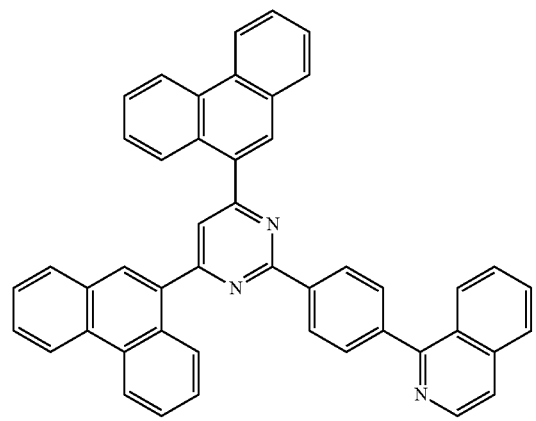
ET25
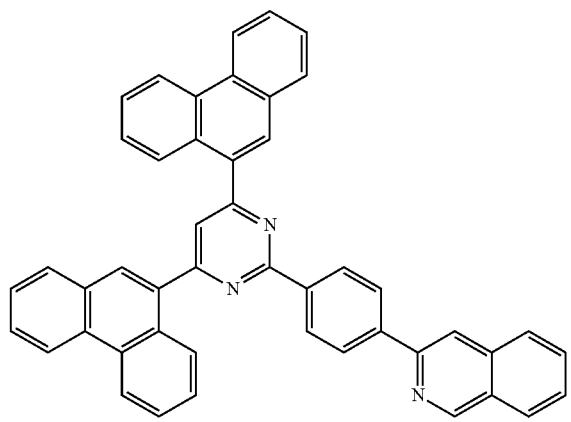
ET26
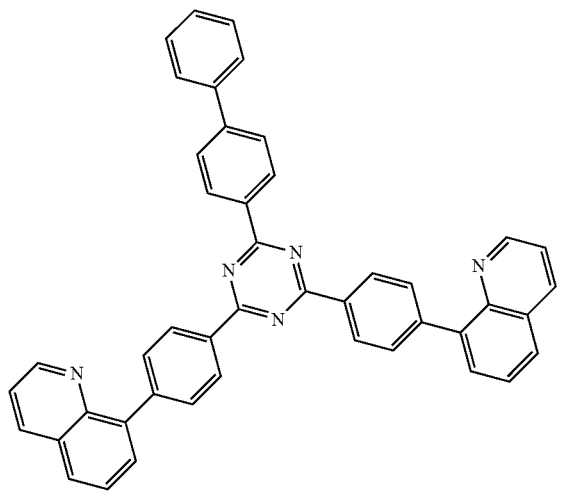
ET27
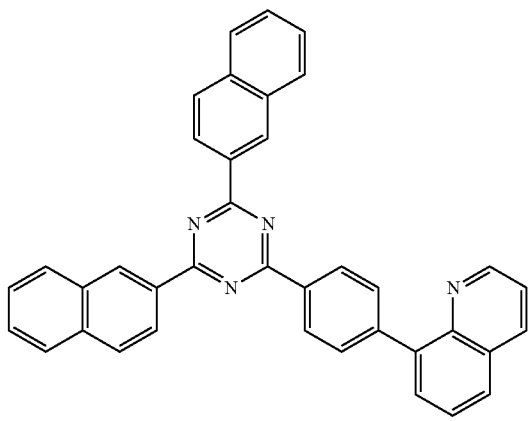
ET28
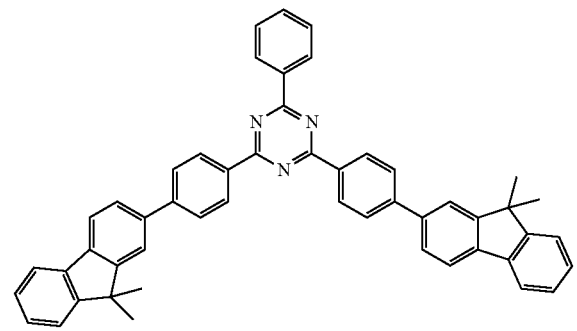

-continued
ET29
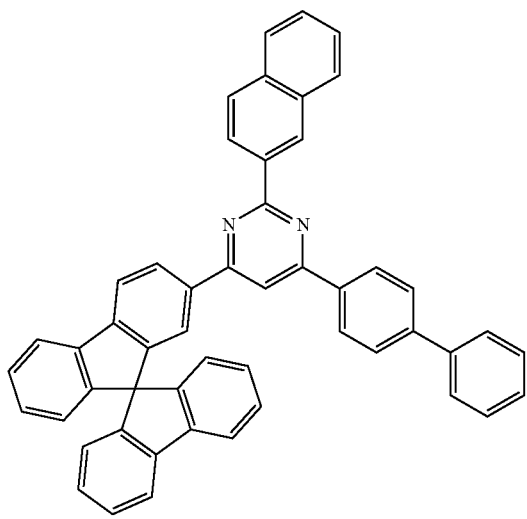
ET30
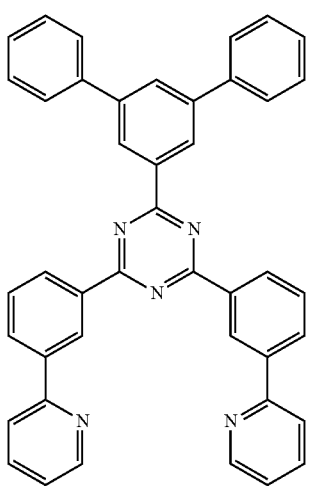
ET31
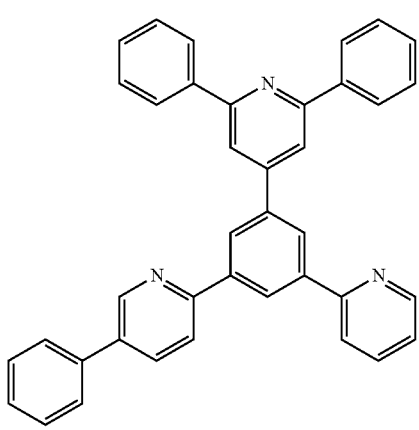
ET32
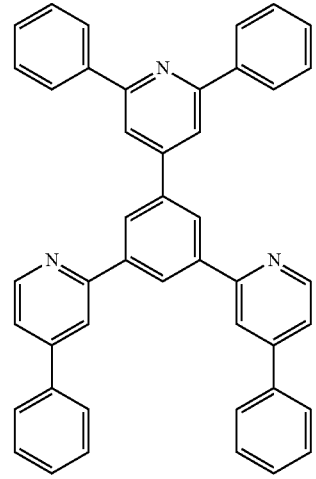
ET33
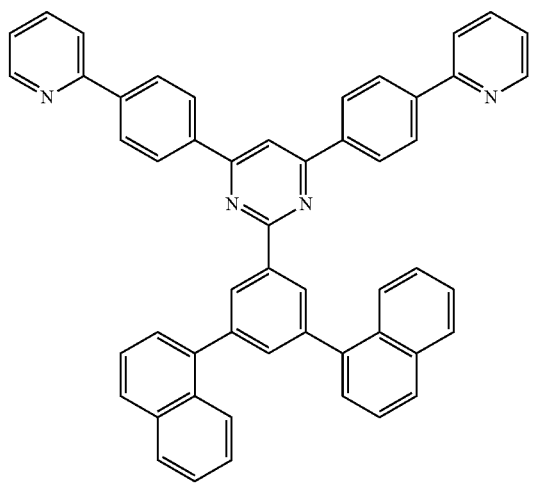
ET34
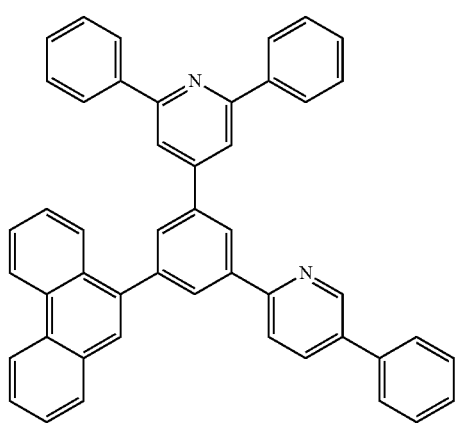

ET35
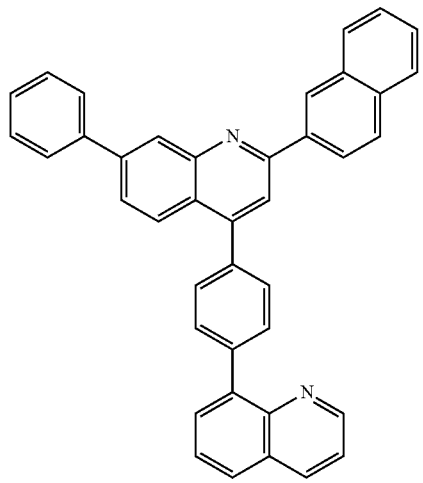
ET36
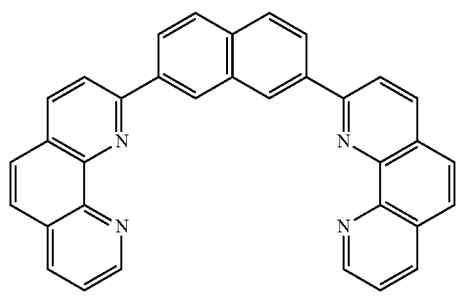
ET37
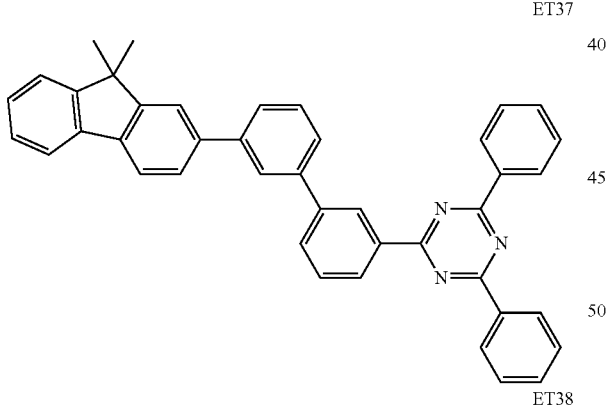
ET38
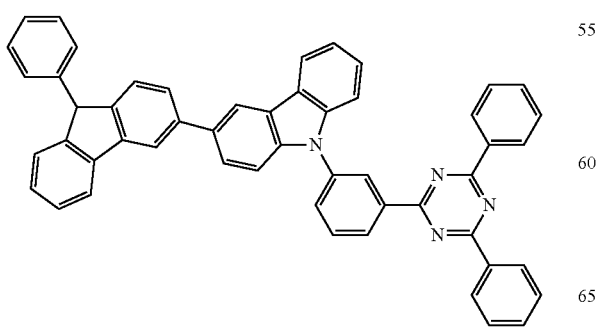
ET39
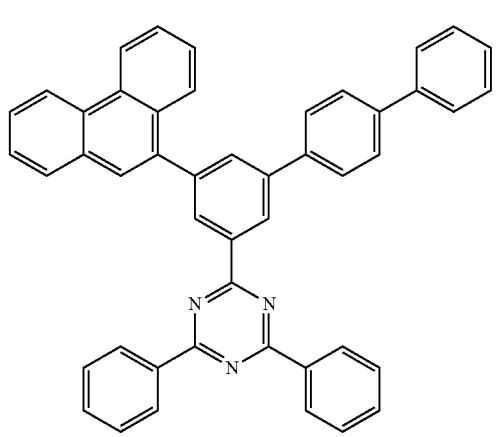
ET40
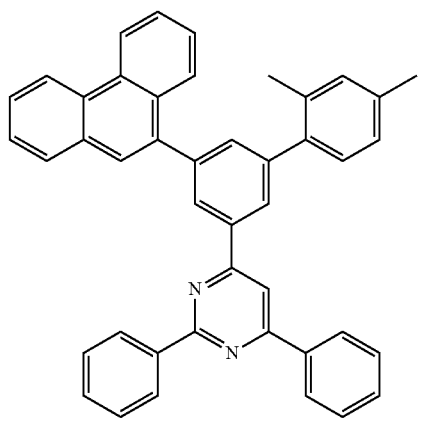
ET41
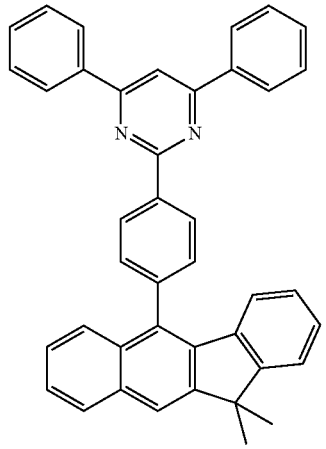

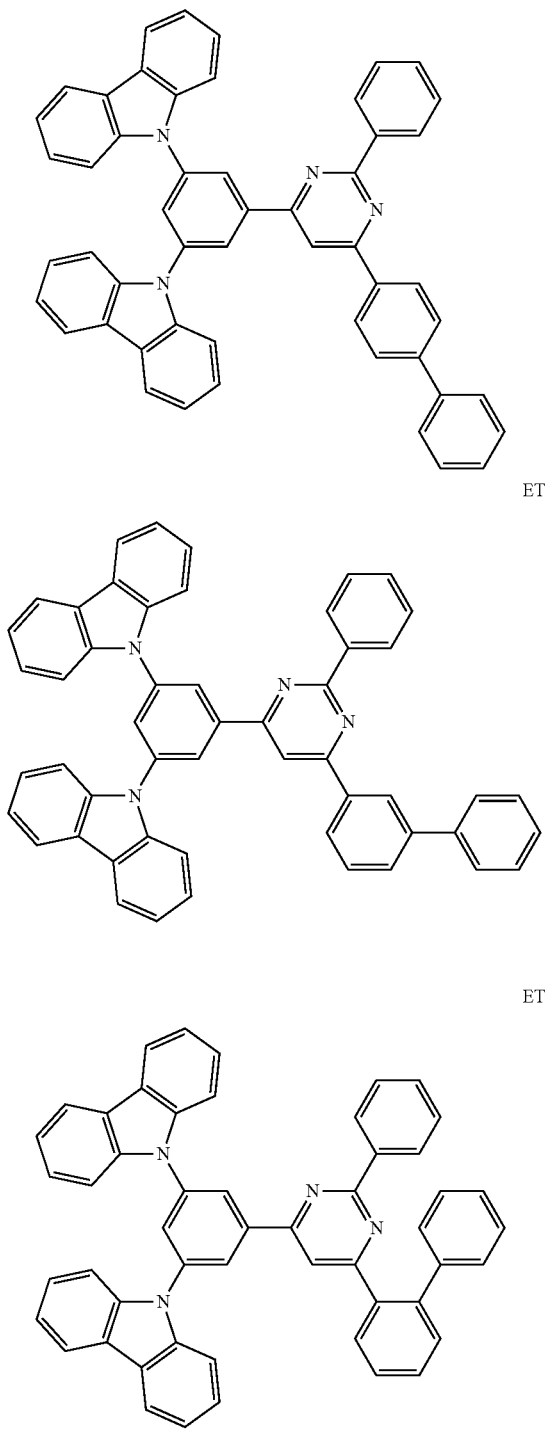

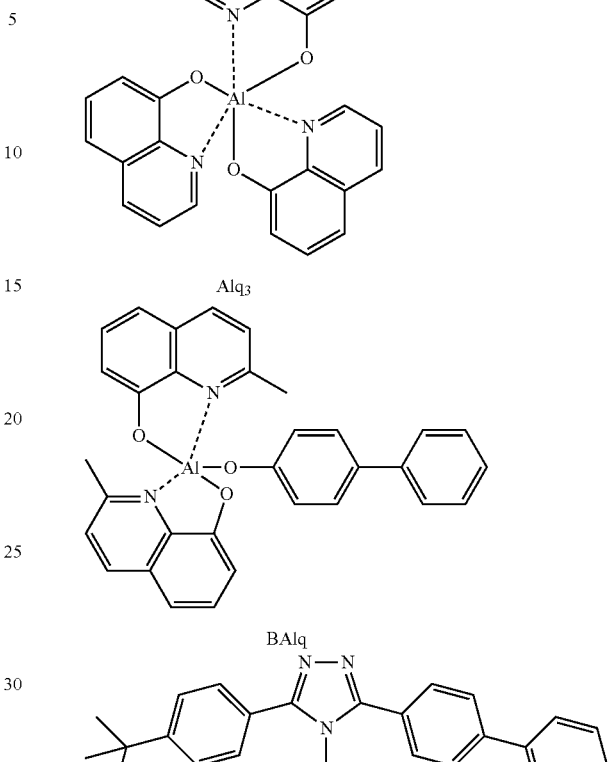

The thickness of the electron transport region may be from about 50 Å to about 5000 Å, for example, from about 100 Å to about 4000 Å. When the electron transport region includes the buffer layer, the hole blocking layer, the electron transport layer, or any combination thereof, the buffer layer and the hole blocking layer may each independently have a thickness of about 20 Å to about 1000 Å, for example, about 30 Å to about 300 Å, and the electron transport layer may have a thickness of about 100 Å to about 1000 Å, or, for example, about 150 Å to about 500 Å. When the thicknesses of the buffer layer, the hole blocking layer and/or the electron transport layer are within these ranges, satisfactory electron transport characteristics may be obtained without a substantial increase in driving voltage. The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (lithium quinolate, LiQ) or ET-D2:

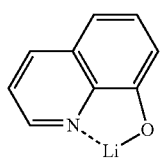

ET-D1

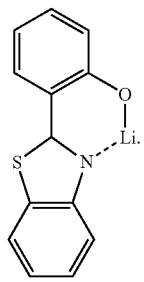

ET-D2

The electron transport region may include an electron injection layer that facilitates the injection of electrons. The electron injection layer may directly contact the second electrode 170. The electron injection layer may have: i) a single-layered structure consisting of a single layer consisting of a single material; ii) a single-layered structure consisting of a single layer consisting of a plurality of different materials; or iii) a multi-layered structure including a plurality of layers including different materials. The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof. The alkali metal-containing compound, the alkaline earth metal-containing compound, and the rare earth metal-containing compound may be: oxides, halides (for example, fluorides, chlorides, bromides, or iodides), or tellurides of the alkali metal, the alkaline earth metal, and the rare earth metal; or any combination thereof.

The alkali metal-containing compound may include: alkali metal oxides such as $Li_2O$, $Cs_2O$, or $K_2O$; alkali metal halides such as LiF, NaF, CsF, KF, LiI, NaI, CsI, or KI; or any combination thereof. The alkaline earth metal-containing compound may include an alkaline earth metal compound, such as BaO, SrO, CaO, $Ba_xSr_{1-x}O$ (wherein x is a real number satisfying the condition of 0<x<1), $Ba_xCa_{1-x}O$ (wherein x is a real number satisfying the condition of 0<x<1), and the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In other embodiments, the rare earth metal-containing compound may include a lanthanide metal telluride. Examples of the lanthanide metal telluride may be LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may each include: i) ions of the alkali metal, the alkaline earth metal, or the rare earth metal; and ii), as a ligand bonded to the metal ions, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

The electron injection layer may consist exclusively of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In one or more embodiments, the electron injection layer may consist of: i) an alkali metal-containing compound (for example, an alkali metal halide); or ii) a) an alkali metal-containing compound (for example, an alkali metal halide) and b) an alkali metal, an alkaline earth metal, a rare earth metal, or any combination thereof. For example, the electron injection layer may be a KI:Yb co-deposited layer, an RbI:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material. The thickness of the electron injection layer may be in a range of about 1 Å to about 100 Å, for example, about 3 Å to about 90 Å. When the thickness of the electron injection layer is within the ranges described above, the electron injection layer may have satisfactory electron injection characteristics without a substantial increase in driving voltage.

Second Electrode 170

The second electrode 170 may be located over the buffer layer 156 or the electron transport region as described above. The second electrode 190 may be a cathode, and as the material for the second electrode 190, a metal, an alloy, an electrically conductive compound, or any combination thereof, each having a low work function, may be used.

The second electrode 170 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), an ITO, an IZO, or any combination thereof. The second electrode 170 may be a transmissive electrode, a semi-transmissive electrode, or a reflective electrode. The second electrode 170 may have a single-layered structure or a multi-layered structure including a plurality of layers.

Capping Layer

A first capping layer may be located outside the first electrode 110, and/or a second capping layer may be located outside the second electrode 170. The first capping layer and/or second capping layer prevents impurities such as water, oxygen, and the like from entering the organic photodetectors 10, 20, and 30, thus improving reliability of the organic photodetectors 10, 20, and 30. The first capping layer and the second capping layer may each include a material having a refractive index of about 1.6 or more (at 589 nanometer (nm)). The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compounds, the heterocyclic compounds, and the amine group-containing compounds may optionally be substituted with a substituent including O, N, S, Se, Si, F, Cl, Br, I, or any combination thereof. In one or more embodiments, at least one of the first capping layer and the second capping layer may each independently include an amine group-containing compound.

In one or more embodiments, at least one of the first capping layer and the second capping layer may each independently include a compound represented by Formula 201, a compound represented by Formula 202, or any combination thereof. In one or more embodiments, at least one of the first capping layer and the second capping layer may each independently include one of Compounds HT28 to HT33, one of Compounds CP1 to CP6, N4,N4'-di(naphthalen-2-yl)-N4,N4'-diphenyl-[1,1'-biphenyl]-4,4'-diamine (β-NPB), or any combination thereof:

CP1

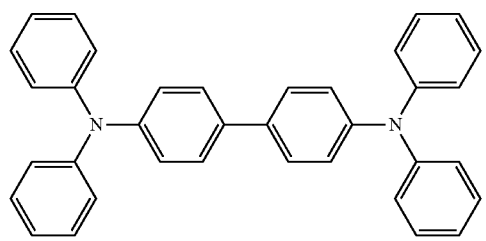

CP2

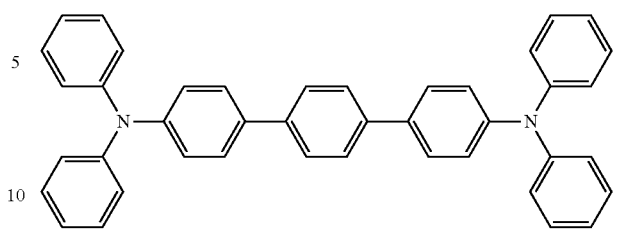

CP3

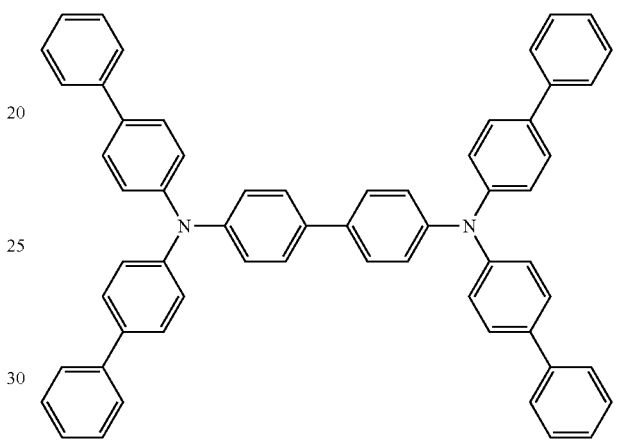

CP4

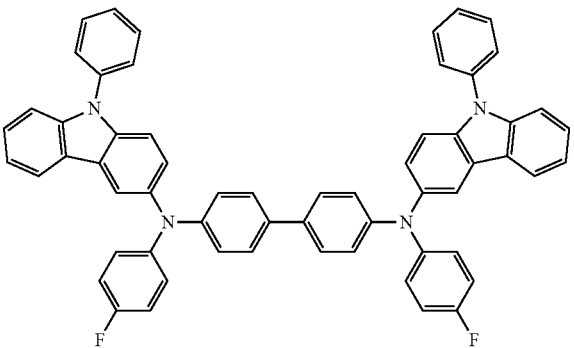

CP5

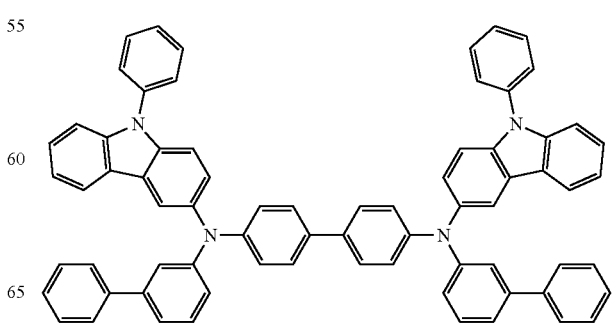

-continued

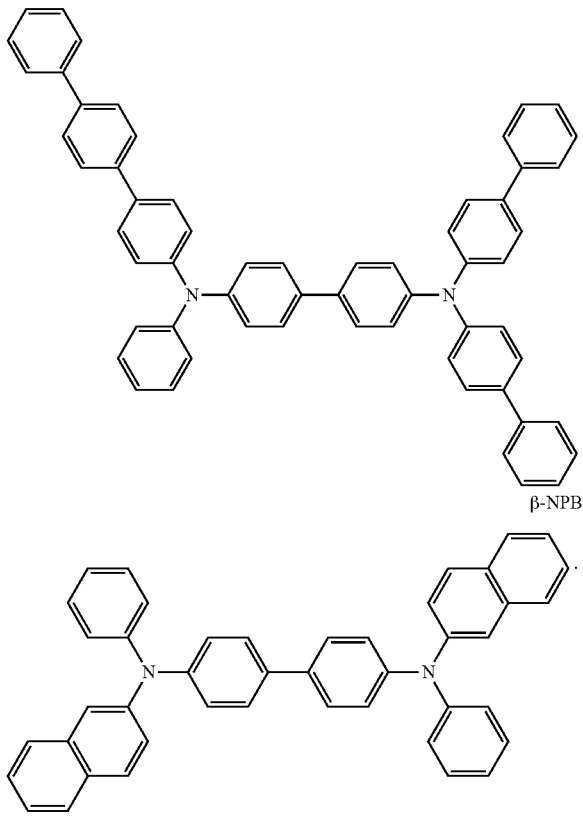

CP6

β-NPB

Electronic Apparatus

An electronic apparatus may include the organic photodetector 10, 20, or 30 as described above. For example, the electronic apparatus may further include a light-emitting device. The electronic apparatus may include: a substrate including a light detection region and an light emission region; an organic photodetector located on the light detection region; and a light-emitting device located on the light emission region, The organic photodetector may include: a first pixel electrode; a second or counter electrode facing the first pixel electrode; and a hole injection layer, a hole transport layer, and an activation layer, which are arranged sequentially between the first pixel electrode and the counter electrode, wherein the hole transport layer may include a first hole transport layer including a p-dopant, and a second hole transport layer not including a p-dopant. The light-emitting device may include: a second pixel electrode; the counter electrode facing the second pixel electrode; and the hole injection layer, the second hole transport layer, and an emission layer, which are arranged sequentially between the second pixel electrode and the counter electrode. The first pixel electrode, the first hole transport layer, and the activation layer are arranged in correspondence with the light detection region. The second pixel electrode and the emission layer may be arranged in correspondence with, i.e., to overlap the light emission region. Furthermore, the hole injection layer, the second hole transport layer, and the counter electrode are located over substantially the entirety of the light detection region and the light emission region.

The electronic apparatus may take the form of or be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 4:
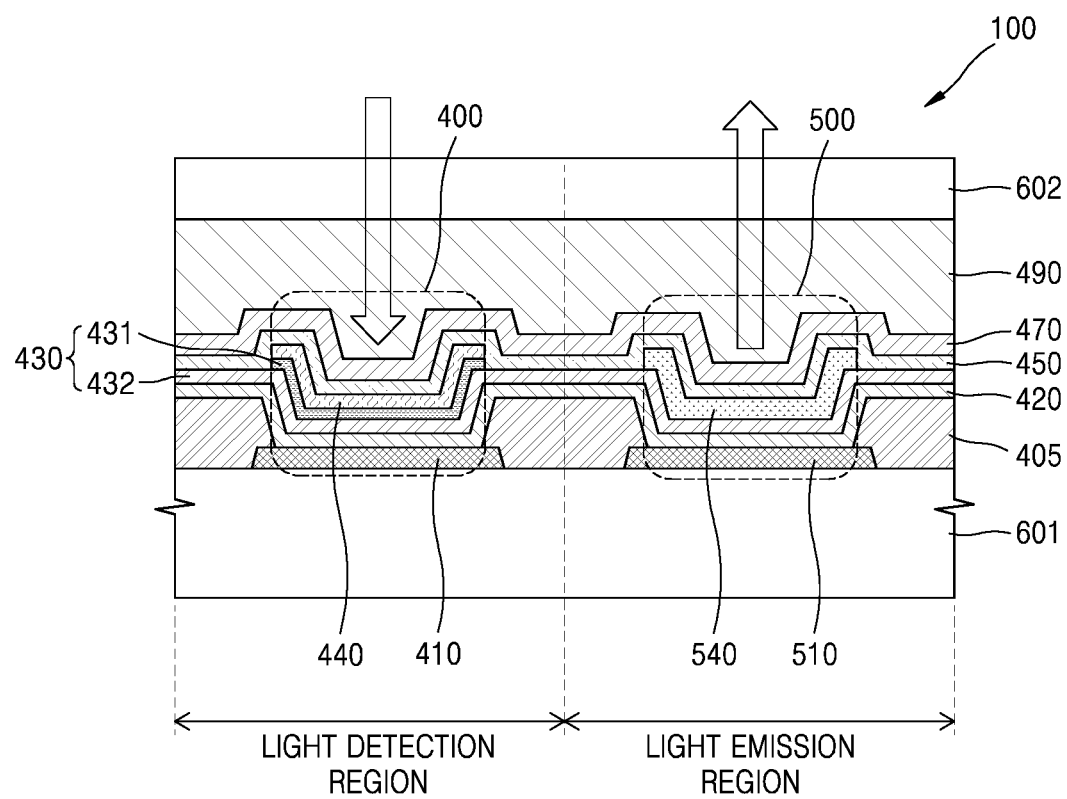
FIG. 4 is a schematic cross-sectional view of an embodiment of an electronic apparatus including an organic photodetector constructed according to the principles of the invention.
Figure 5:
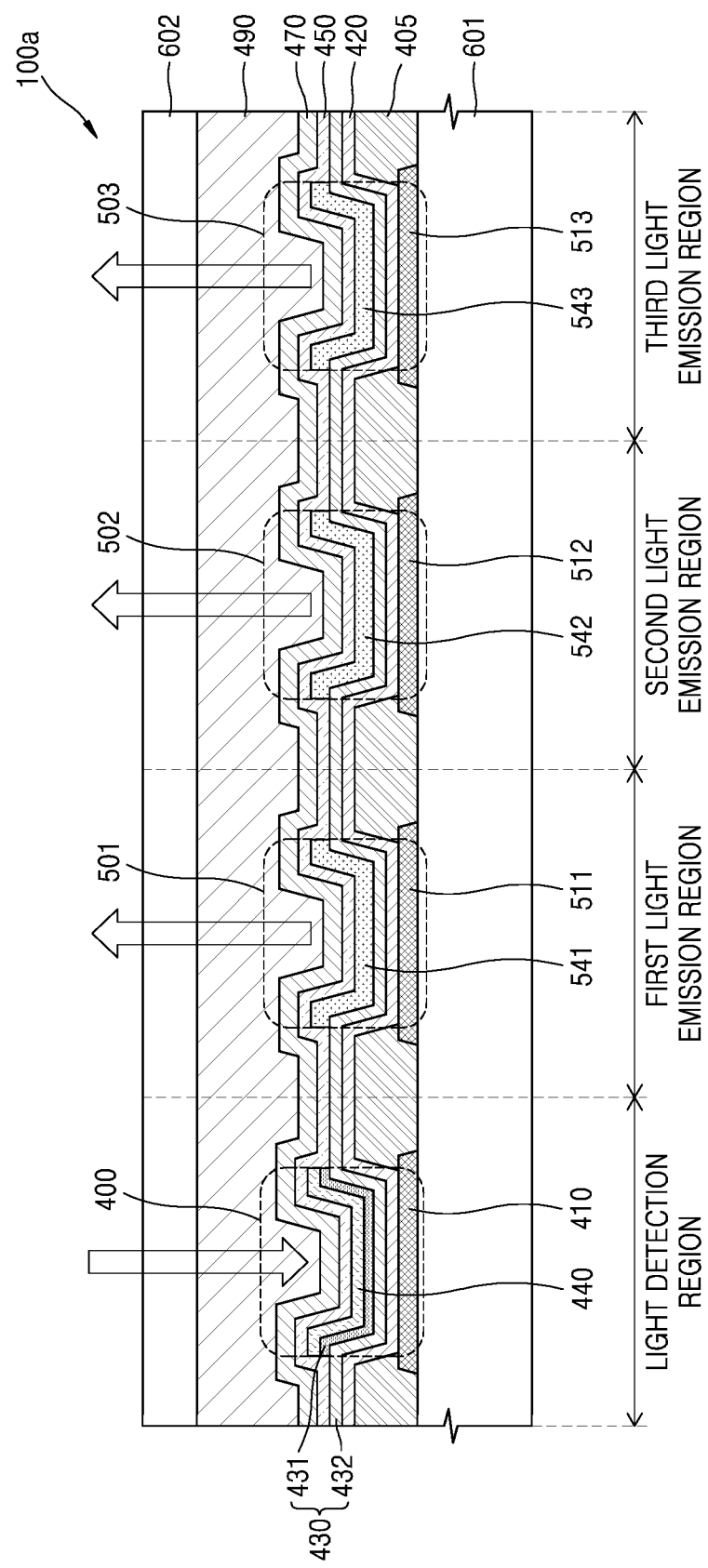
FIG. 5 is a schematic cross-sectional view of another embodiment of an electronic apparatus including an organic photodetector constructed according to the principles of the invention.

Description of FIGS. 4 and 5

FIG. 4 is a schematic cross-sectional view of an embodiment of an electronic apparatus including an organic photodetector constructed according to the principles of the invention.

Referring to FIG. 4, the electronic apparatus 100 includes an organic photodetector 400 and a light-emitting device 500 between a substrate 601 and a substrate 602. The substrate 601 and the substrate 602 may be a flexible substrate, a glass substrate, or a metal substrate. A buffer layer and a thin-film transistor may be located on the substrate 601.

The buffer layer serves to prevent infiltration of impurities through the substrate 601 and provide a substantially flat surface on the substrate 601. The thin-film transistor is located on the buffer layer, and may include an activation layer, a gate electrode, a source electrode, and a drain electrode.

The thin-film transistor is electrically connected to the light-emitting device 500 to drive the light-emitting device. A second pixel electrode 510 of the light-emitting device 500 may be electrically connected with either one of the source electrode and the drain electrode. Another thin-film transistor may be electrically connected to the organic photodetector 400. A first pixel electrode 410 of the organic photodetector 400 may be electrically connected with either one of the source electrode and the drain electrode.

The organic photodetector 400 may include the first pixel electrode 410, a hole injection layer 420, a first hole transport layer 431, a second hole transport layer 432, an activation layer 440, an electron transport layer 450, and a counter electrode 470.

In one or more examples, the first pixel electrode 410 may be an anode, and the counter electrode 470 may be a cathode. That is, as the organic photodetector 400 is driven by applying a reverse bias across the first pixel electrode 410 and the counter electrode 470, the electronic apparatus 100 may detect light incident onto the organic photodetector 400, generate charges, and extract the charges as a current.

The light-emitting device 500 may include the second pixel electrode 510, the hole injection layer 420, the second hole transport layer 432, an emission layer 540, an electron transport layer 450, and the counter electrode 470.

In one or more examples, the second pixel electrode 510 may be an anode, and the counter electrode 470 may be a cathode. That is, in the light-emitting device 500, holes injected from the second pixel electrode 510 and electrons injected from the counter electrode 470 recombine in the emission layer 540 to generate excitons, which generate light by changing from an excited state to a ground state. Descriptions of the first pixel electrode 410 and the second pixel electrode 510, and descriptions on the first electrode 110 may be the same as those referenced herein.

A pixel define layer 405 is formed at the edge portions of the first pixel electrode 410 and the second pixel electrode 510. The pixel define layer 405 defines a pixel region, and may electrically insulate the first pixel electrode 410 and the second pixel electrode 510. The pixel define layer 405 may include, for example, known various organic insulating material (for example, silicone-based materials, and the like), inorganic insulating materials, or organic/inorganic composite insulating materials. The pixel define layer 405 may be a transmissive film that transmits visible light, or a blocking film that blocks visible light.

The hole injection layer 420 and the second hole transport layer 432, which are common layers, are formed sequentially on the first pixel electrode 410 and the second pixel electrode 510. Descriptions of the hole injection layer 420 and second hole transport layer 432 may be the same as those referenced herein.

The first hole transport layer 431, which overlaps the light detection region, is formed on the second hole transport layer 432. For descriptions of the first hole transport layer 431, related descriptions provided herein may be referenced.

Although, for the sake of convenience, FIG. 4 illustrates the electronic apparatus 100 as having the first hole transport layer 431 located between the first hole transport layer 432 and the activation layer 440, embodiments are not limited thereto. The first hole transport layer 431 may inserted in the middle of the second hole transport layer 432, or may be located between the hole injection layer 420 and the second hole transport layer 432.

The activation layer 440 is formed on the first hole transport layer 430 overlapping the light detection region. Descriptions of the activation layer 440 may be referenced herein.

The emission layer 540 is formed on the second hole transport layer 432 to overlap the emission area. For descriptions of the emission layer 540, related descriptions may be referenced herein. In one or more embodiments, the light-emitting device 500 may further include, between the second pixel electrode 510 and the emission layer 540, an electron blocking layer arranged to overlap the light emission region.

As common layers for the entirety of the light detection region and light emission region, the electron transport layer 450 and the counter electrode 470 are sequentially formed on the activation layer 440 and the emission layer 540. Descriptions of the electron transport layer 450 and the counter electrode 470 and descriptions of the electron transport layer 130 and the second electrode 170 may be referenced herein.

The hole injection layer 420, the second hole transport layer 432, and the electron transport layer 450 may each overlap at least substantially the entirety of the light detection region and the light emission region. In other embodiments, at least one of the hole injection layer 420, the second hole transport layer 432, and the electron transport layer 450 may be arranged to overlap either one of the light detection region and the light emission region. When the second hole transport layer 432 overlaps the light emission region, the second hole transport layer 432 of the light-emitting device 500 that overlaps the light emission region may further include a p-dopant.

As such, the manufacturing process of the electronic apparatus 100 may be simplified by arranging common layers for the organic photodetector 400 and the light-emitting device 500, existing functional layer materials used in the light-emitting device 500 can also be used for the organic photodetector 400, and thus, the organic photodetector 400 may be provided in-pixel in the electronic apparatus. In one or more embodiments, an electron injection layer may be further included between the electron transport layer 450 and the counter electrode 470.

A capping layer may be located on the counter electrode 470. A material that can be used for the capping layer may include an organic material and/or inorganic material as described above. The capping layer may facilitate efficient emission of light generated from the light-emitting device 500, in addition to having a protective function for the organic photodetector 400 and the light-emitting device 500.

An encapsulation portion 490 may be located on the capping layer. The encapsulation portion 490 may be located on the organic photodetector 400 and the light-emitting device 500 to protect the organic photodetector 400 and the light-emitting device 500 from mixture or oxygen. The encapsulation portion 490 may include: an inorganic film including a silicon nitride ($SiN_x$), a silicon oxide ($SiO_x$), an indium tin oxide, an indium zinc oxide, or any combination thereof; an organic film including a polyethylene terephthalate, a polyethylene naphthalate, a polycarbonate, a polyimide, a polyethylene sulfonate, a polyoxymethylene, a polyarylate, a hexamethyldisiloxane, an acrylic resin (for example, a polymethyl methacrylate, a polyacrylic acid, or the like), an epoxy-based resin (for example, an aliphatic glycidyl ether (AGE), or the like), or any combination thereof; or a combination of the inorganic film and the organic film. The electronic apparatus 100 may be, for example, a display apparatus. The electronic apparatus 100 includes both the organic photodetector 400 and the light-emitting device 500, and thus, may be a display apparatus with a light detection function.

FIG. 5 is a schematic cross-sectional view of another embodiment of an electronic apparatus including an organic photodetector constructed according to the principles of the invention.

Although FIG. 4 illustrates the electronic apparatus 100 as including one light-emitting device 500, another electronic apparatus 100a may include, as illustrated in FIG. 5, an organic photodetector 400, a first light-emitting device 501, a second light-emitting device 502, and a third light-emitting device 503. Constituent elements of the electronic apparatus 100a that are the same as those of the electronic apparatus 100 of FIG. 4 will be understood with reference to the descriptions of the electronic apparatus 100 and not described again to avoid redundancy.

The first light-emitting device 501 may include a second pixel electrode 511, the hole injection layer 420, the second hole transport layer 432, a first emission layer 541, the electron transport layer 450, and the counter electrode 470. The second light-emitting device 502 may include a third pixel electrode 512, the hole injection layer 420, the second hole transport layer 432, a second emission layer 542, the electron transport layer 450, and the counter electrode 470. The third light-emitting device 503 may include a fourth pixel electrode 513, the hole injection layer 420, the second hole transport layer 432, a third emission layer 543, the electron transport layer 450, and the counter electrode 470.

The second pixel electrode 511, the third pixel electrode 512, and the fourth pixel electrode 513 are arranged to correspond to a first light emission region, a second light emission region, and a third light emission region, respectively, and will be understood with reference to the descriptions of the first electrode 110 provided herein. The first emission layer 541 overlaps the first light emission region and emits a first color light, the second emission layer 542 overlaps the second light emission region and emits a second color light, and the third emission layer 543 overlaps the third light emission region and emits a third color light.

A maximum emission wavelength of the first color light, a maximum emission wavelength of the second color light, and a maximum emission wavelength of the third color light may be identical to or different from each other. For example, the maximum emission wavelength of the first color light and the maximum emission wavelength of the second color light may each be greater than the maximum emission wavelength of the third color light.

For example, the first color light may be red light, the second color light may be green light, and the third color light may be blue light, but embodiments are not limited thereto. Accordingly, the electronic apparatus 100a is capable of full-color emission. The first color light, the second color light, and the third color light are not limited to red light, green light, and blue light, respectively, and may be any combination of light of different colors, as long as mixed light thereof is white light.

The organic photodetector 400, the first light-emitting device 501, the second light-emitting device 502, and the third light-emitting device 503 may be subpixels constituting a single pixel. In one or more embodiments, the single pixel may include at least one organic photodetector 400. The electronic apparatus 100a may be a display apparatus. The electronic apparatus 100a includes the organic photodetector 400 and the first light-emitting device 501, the second light-emitting device 502, and the third light-emitting device 503, and thus, may be a full-color display apparatus with a light detection function.

Figure 6A:
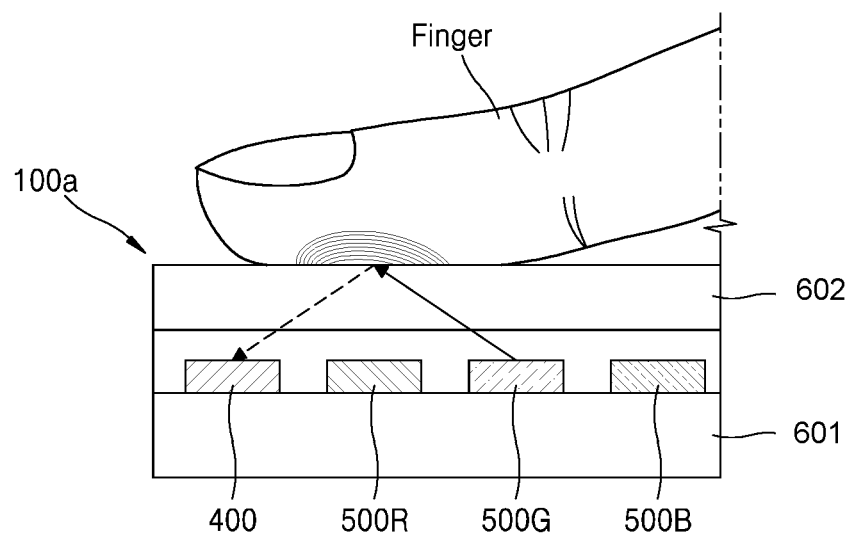
FIG. 6A is a schematic cross-sectional diagram of an embodiment of an application of an electronic apparatus constructed according to the principles of the invention.
Figure 6B:
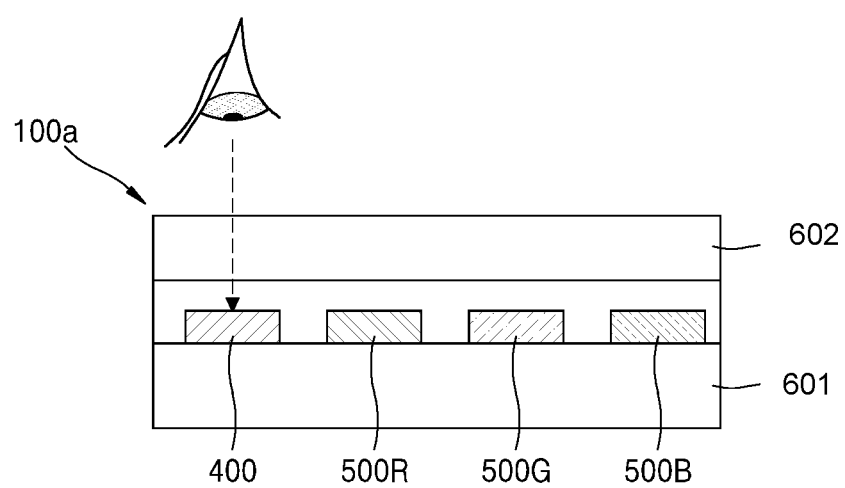
FIG. 6B is a schematic cross-sectional diagram of another embodiment of an application of an electronic apparatus constructed according to the principles of the invention.

Descriptions of FIGS. 6A and 6B

FIG. 6A is a schematic cross-sectional diagram of an embodiment of an application of an electronic apparatus constructed according to the principles of the invention. FIG. 6B is a schematic cross-sectional diagram of another embodiment of an application of an electronic apparatus constructed according to the principles of the invention.

In an electronic apparatus 100a illustrated in FIG. 6A, an organic photodetector 400 and light-emitting devices 501, 502, and 503 are located between a substrate 601 and a substrate 602. For example, red light, green light, and blue light may be emitted from the light-emitting device 501, the light-emitting device 502, and the light-emitting device 503, respectively.

The electronic apparatus 100a may have a function to detect, for example, the fingerprint of a finger, which is an object in contact with the electronic apparatus. For example, as illustrated in FIG. 6A, at least a portion of the reflected light, which is reflected from the fingerprint of a user, of the light emitted from the light-emitting device 502 of FIG. 5 is incident onto the organic photodetector 400 again, and thus, the organic photodetector 400 may detect the reflected light. Ridges in the fingerprint pattern of a finger are in close contact with the substrate 602, and thus, the organic photodetector 400 may acquire the fingerprint pattern of the user. Although FIG. 6A illustrates an embodiment in which information about the object in contact with the electronic apparatus 100a is obtained with the light emitted from the light-emitting device 502, the same as described above may apply even in the case of obtaining information using the light emitted from the light-emitting device 501 and/or light-emitting device 503 of FIG. 5.

In addition, as illustrated in FIG. 6B, an electronic apparatus 100a may detect an object not in contact with the electronic apparatus 100a. In this specific embodiment, the object may be an eye, in particular, the retina of an eye.

Manufacture Method

The layers included in the hole transport region, the activation layer, and the layers included in the electron transport region may be formed in certain regions by using one or more suitable methods selected from vacuum deposition, spin coating, casting, Langmuir-Blodgett (LB) deposition, ink-jet printing, laser-printing, and laser-induced thermal imaging (LITI).

When the layers of the hole transport region, the activation layer, and the layers of the electron transport region are formed by vacuum deposition, deposition conditions may be selected from within a deposition temperature of about 100° C. to about 500° C., a vacuum degree of about $10^{-8}$ torr to about $10^{-3}$ torr, and a deposition rate of about 0.01 angstrom per second (Å/sec) to about 100 Å/sec, in consideration of the material and structure of a layer to be formed.

DEFINITION OF TERMS

As used herein, a "p-type" may mean, e.g., a layer or a semiconductor doped with an element, such as boron, with three valence electrons integrated into the lattice structure of the layer or semiconductor.

As used herein, an "n-type" may mean, e.g., a layer or a semiconductor doped with an element, such as phosphorus, with five valence electrons integrated into the lattice structure of the layer or semiconductor.

As used herein, a "PN junction" may mean a boundary or interface between two types of semiconductor materials, p-type and n-type, inside a layer or a semiconductor.

As used herein, the term "atom" may mean an element or its corresponding radical bonded to one or more other atoms.

The terms "hydrogen" and "deuterium" refer to their respective atoms and corresponding radicals with the deuterium radical abbreviated "-D", and the terms "—F, —Cl, —Br, and —I" are radicals of, respectively, fluorine, chlorine, bromine, and iodine.

As used herein, a substituent for a monovalent group, e.g., alkyl, may also be, independently, a substituent for a corresponding divalent group, e.g., alkylene.

As used herein, the term "energy level" may be expressed in "electron volts" and "energy level" and "electron volt" may be abbreviated, independently, as "eV".

As used herein, the term "fused" may refer to a ring having one or more sides in common with another ring, and includes a fused ring.

The term "$C_3$-$C_{60}$ carbocyclic group" as used herein refers to a cyclic group of 3-60 carbon atoms consisting of carbons only as a ring-forming atom, and the term "$C_1$-$C_{60}$ heterocyclic group" as used herein refers to a cyclic group of 1-60 carbon atoms that further includes, in addition to carbon, a heteroatom as ring-forming atoms. The $C_3$-$C_{60}$ carbocyclic group and the $C_1$-$C_{60}$ heterocyclic group may each be a monocyclic group consisting of one ring or a polycyclic group in which two or more rings are fused with each other. For example, the $C_1$-$C_{60}$ heterocyclic group has 3 to 61 ring-forming atoms.

The "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group of 3-60 carbon atoms, excluding *—N=*' as a ring-forming moiety, and the term "π electron-deficient nitrogen-containing $C_1$-$C_{60}$ cyclic group" as used herein refers to a heterocyclic group of 1-60 carbon atoms, including *—N=*' as a ring-forming moiety.

For example, the $C_3$-$C_{60}$ carbocyclic group may be i) a group T1 or ii) a fused cyclic group in which at least two groups T1 are fused with each other, for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spirobifluorene group, a benzofluorene group, an indenophenanthrene group, or an indenoanthracene group.

The $C_1$-$C_{60}$ heterocyclic group may be i) a group T2, ii) a fused cyclic group in which at least two groups T2 are fused with each other, or iii) a fused cyclic group in which at least one group T2 and at least one group T1 are fused with each other, for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The π electron-rich $C_3$-$C_{60}$ cyclic group may be i) a group T1, ii) a fused cyclic group in which at least two groups T1 are fused with each other, iii) a group T3, iv) a fused cyclic group in which at least two groups T3 are fused with each other, or v) a fused cyclic group in which at least one group T3 and at least one group T1 are fused with each other, for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.

The π electron-deficient nitrogen-containing $C_1$-$C_{60}$ cyclic group may be i) a group T4, ii) a fused cyclic group in which at least two groups T4 are fused with each other, iii) a fused cyclic group in which at least one group T4 and at least one T1 group are fused with each other, iv) a fused cyclic group in which at least one group T4 and at least one group T3 are fused with each other, or v) a fused cyclic group in which at least one group T4, at least one group T1, and at least one group T3 are fused with one another, for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.

The group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group.

The group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group.

The group T3 may be a furan group, a thiophene group, a 1H-pyrrole group, a silole group, or a borole group.

The group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{60}$ heterocyclic group, the π electron-rich $C_3$-$C_{60}$ cyclic group, or the π electron-deficient nitrogen-containing $C_1$-$C_{60}$ cyclic group" as used herein refer to a group fused with any cyclic group, a monovalent group, or a polyvalent group (for example, a divalent group, a trivalent group, a tetravalent group, etc.), depending on the structure of a formula in connection with which the terms are used. In one or more embodiments, "a benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group are a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic fused polycyclic group, and a monovalent non-aromatic fused heteropolycyclic group. Examples of the divalent $C_3$-$C_{60}$ carbocyclic group and the divalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic fused polycyclic group, and a divalent non-aromatic fused heteropolycyclic group.

The term "$C_1$-$C_{60}$ alkyl group" as used herein refers to a linear or branched aliphatic hydrocarbon monovalent group that has one to sixty carbon atoms, and examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an iso-nonyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having a structure corresponding to the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof are an ethenyl group, a propenyl group, and a butenyl group. The term "$C_2$-$C_{60}$ alkenylene group" as used herein refers to a divalent group having a structure corresponding to the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by —O$A_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group of 3 to 10 carbon atoms, and examples thereof are a cyclopropyl group, a cyclobutyl group, a cyclopentyl group, a cyclohexyl group, a cycloheptyl group, a cyclooctyl group, an adamantyl group, a norbornyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom as a ring-forming atom and has one to ten carbon atoms, and examples thereof are a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to the $C_1$-$C_{10}$ heterocycloalkyl group.

The term $C_3$-$C_{10}$ cycloalkenyl group used herein refers to a monovalent cyclic group that has three to ten carbon atoms and at least one carbon-carbon double bond in the ring thereof and no aromaticity, and examples thereof are a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom as a ring-forming atom, one to ten carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having a structure corresponding to the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group are a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be fused with each other.

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom as a ring-forming atom, and one to sixty carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be fused with each other.

The term "monovalent non-aromatic fused polycyclic group" as used herein refers to a monovalent group having two or more rings fused with each other, only carbons as ring-forming atoms (for example, 8 to 60 carbon atoms), and having non-aromaticity throughout its entire molecular structure. Examples of the monovalent non-aromatic fused polycyclic group are an indenyl group, a fluorenyl group, a spiro-bifluorenyl group, a benzofluorenyl group, an indenophenanthrenyl group, and an indenoanthracenyl group. The term "divalent non-aromatic fused polycyclic group" as used herein refers to a divalent group having a structure corresponding to a monovalent non-aromatic fused polycyclic group.

The term "monovalent non-aromatic fused heteropolycyclic group" as used herein refers to a monovalent group having two or more rings fused to each other, at least one heteroatom, in addition to carbon atoms (for example, including 2 to 60 carbon atoms), as a ring-forming atom, and no aromaticity in its entire molecular structure. Examples of the monovalent non-aromatic fused heteropolycyclic group are 9,9-dihydroacridinyl group, 9H-xanthenyl group, and the like. The term "divalent non-aromatic fused heteropolycyclic group" as used herein refers to a divalent group having a structure corresponding to a monovalent non-aromatic fused heteropolycyclic group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_7$-$C_{60}$ aryl alkyl group" used herein refers to -$A_{104}A_{105}$ (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" used herein refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:
deuterium (-D), —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof.

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

The variables $Q_1$ to $Q_3$, $Q_{11}$ to $Q_{13}$, $Q_{21}$ to $Q_{23}$, and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, a $C_7$-$C_{60}$ aryl alkyl group, or a $C_2$-$C_{60}$ heteroaryl alkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "heteroatom" as used herein refers to any atom other than a carbon atom. Examples of the heteroatom are O, S, N, P, Si, B, Ge, Se, and any combination thereof The term "the third-row transition metal" as used herein includes hafnium (Hf), tantalum (Ta), tungsten (W), rhenium (Re), osmium (Os), iridium (Ir), platinum (Pt), gold (Au), and the like.

As used herein, the term "Ph" refers to a phenyl group, the term "Me" refers to a methyl group, the term "Et" refers to an ethyl group, the term "ter-Bu" or "Bu$^t$" refers to a tert-butyl group, and the term "OMe" refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

EXAMPLES

Comparative Example 1

An ITO glass substrate (anode) was cut to a size of 50 millimeter (mm)×50 mm×0.7 mm, ultrasonically cleaned with isopropyl alcohol and pure water each for 15 minutes, and then cleaned by irradiation of ultraviolet rays and exposure to ozone for 10 minutes. Next, the ITO substrate was loaded into a vacuum deposition apparatus. The compound HAT-CN was vacuum-deposited on the anode to form a hole injection layer of a thickness of 100 Å, and HT3 was vacuum-deposited on the hole injection layer to form a hole transport layer of a thickness of 1250 Å.

The compound SubPC of a thickness of 200 Å and C60 fullerene of a thickness 250 Å were co-deposited or deposited sequentially on the hole transport layer to form an activation layer. Subsequently, BAlq was vacuum-deposited to form a hole blocking layer of a thickness of 50 Å, and ET1 was vacuum-deposited on the hole blocking layer to form an electron transport layer of a thickness of 300 Å.

The compound 8-hydroxy-lithium quinolate (LiQ) of a thickness of 10 Å and the alloy MgAg of a thickness of 100 Å were deposited sequentially on the electron transport layer to form a cathode, thereby manufacturing an organic photodetector.

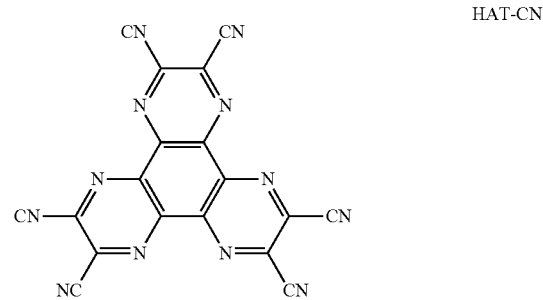

HAT-CN

-continued

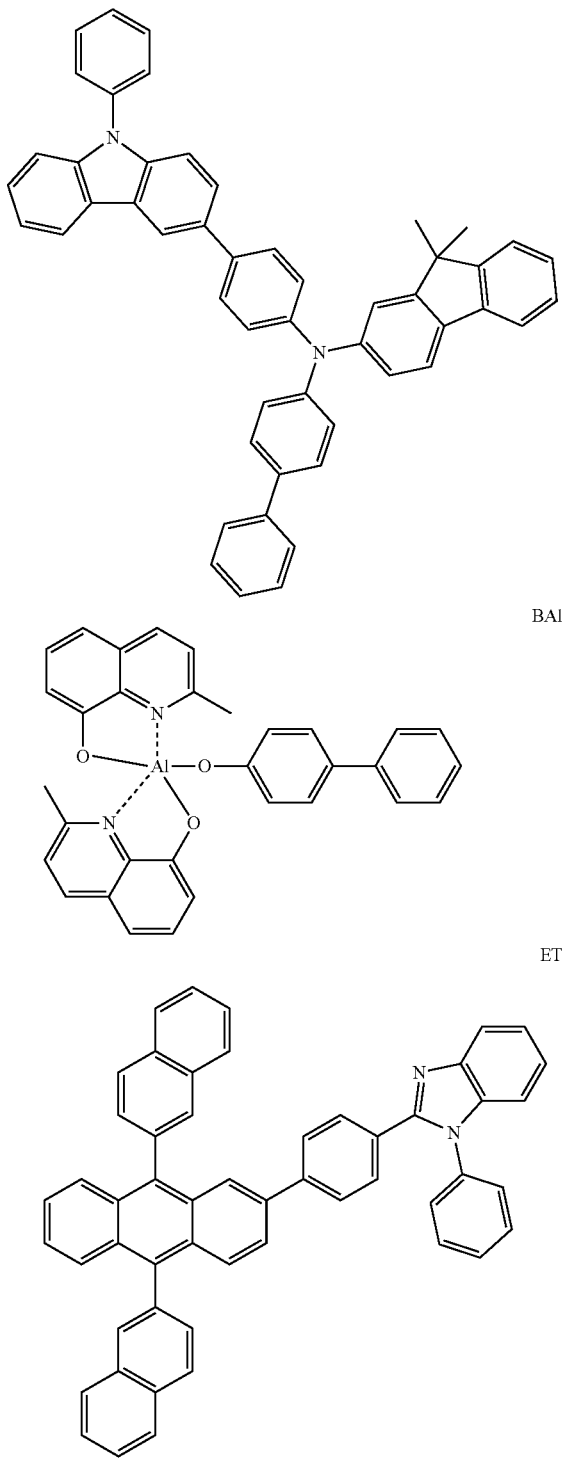

HT3

BAlq

ET1

Example 1

An organic photodetector was manufactured in the same manner as in Comparative Example 1, except that, between the hole injection layer and the hole transport layer, a p-type hole transport layer was further formed by co-deposition of HT3 and HAT-CN (with a HAT-CN doping concentration of 1 vol. %) to a thickness of 100 Å.

Example 2

An organic photodetector was manufactured in the same manner as in Comparative Example 1, except that HT3 of 500 Å, HT3:HAT-CN (with a HAT-CN doping concentration of 1 vol. %) of 100 Å, and HT3 of 750 Å were formed sequentially to form the hole transport layer.

Example 3

An organic photodetector was manufactured in the same manner as in Comparative Example 1, except that HT3 of 1,000 Å and HT3: HAT-CN (with a HAT-CN doping concentration of 1 vol. %) of 100 Å, and HT3 of 250 Å were sequentially formed to form the hole transport layer.

Example 4

An organic photodetector was manufactured in the same manner as in Comparative Example 1, except that, between the hole transport layer and the activation layer, a p-type hole transport layer was further formed by co-deposition of HT3 and HAT-CN (with a HAT-CN doping concentration of 1 vol. %) to a thickness of 100 Å.

Example 5

An organic photodetector was manufactured in the same manner as in Example 3, except that a HAT-CN doping concentration of 0.5 vol. % was applied.

Example 6

An organic photodetector was manufactured in the same manner as in Example 3, except that a HAT-CN doping concentration of 2 vol. % was applied.

Example 7

An organic photodetector was manufactured in the same manner as in Example 3, except that a HAT-CN doping concentration of 4 vol. % was applied.

External quantum efficiencies (EQE) at a wavelength of 530 nm of the organic photodetectors manufactured in Comparative Example 1 and Examples 1 to 7, and dark current densities with a reverse bias of −3V were measured, by applying a voltage to the anode in a dark room and measuring the current. The results are shown in Table 1.

TABLE 1

| Examples | EQE percent (%) @530 nm | Dark current density (mA/cm$^2$) |
|---|---|---|
| Comparative Example 1 | <1% | $2.0*10^{-6}$ |
| Example 1 | 14% | $4.4*10^{-6}$ |
| Example 2 | 16% | $1.7*10^{-5}$ |
| Example 3 | 18% | $1.7*10^{-5}$ |
| Example 4 | 3% | $3.0*10^{-6}$ |
| Example 5 | 12% | $1.2*10^{-5}$ |
| Example 6 | 20% | $2.3*10^{-5}$ |
| Example 7 | 25% | $3.8*10^{-5}$ |

The results summarized in Table 1 show that the organic photodetectors of Examples 1 to 7 exhibited a dark current density of $1 \times 10^{-4}$ mA/cm$^2$ or less and had significantly and unexpectedly improved external quantum efficiencies, as compared with that of the organic photodetector of Comparative Example 1, and thus, had significantly and unexpectedly excellent light detection efficiencies. As described above, according to the one or more embodiments, the organic photodetector may have improved external quantum efficiency, and thus, may have excellent light detection efficiency.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An organic photodetector comprising:
a first electrode;
a second electrode facing the first electrode;
an activation layer between the first electrode and the second electrode;
a hole injection layer between the first electrode and the activation layer; and
a hole transport layer between the hole injection layer and the activation layer,
wherein the hole transport layer comprises: a first hole transport layer including a p-dopant; and a second hole transport layer not including a p-dopant.

2. The organic photodetector of claim 1, wherein the first hole transport layer is disposed in the middle of the second hole transport layer, and
a distance between a surface of the first electrode facing the second electrode and a surface of the first hole transport layer facing the first electrode is about 450 Å to about 1200 Å.

3. The organic photodetector of claim 2, wherein the distance between the surface of the first electrode facing the second electrode and the surface of the first hole transport layer facing the first electrode is about 450 Å to about 650 Å, or about 900 Å to about 1200 Å.

4. The organic photodetector of claim 1, wherein the first hole transport layer is between the hole injection layer and the second hole transport layer, and the hole injection layer and the second hole transport layer are in direct contact with each other.

5. The organic photodetector of claim 1, wherein the first hole transport layer is between the second hole transport layer and the activation layer, and the second hole transport layer and the activation layer are in direct contact with each other.

6. The organic photodetector of claim 1, wherein the p-dopant comprises a compound having a lowest unoccupied molecular orbital energy level of less than about −3.5 eV.

7. The organic photodetector of claim 1, wherein the first hole transport layer further comprises a hole transport material.

8. The organic photodetector of claim 7, wherein the hole transport material comprises a compound of Formula 202 or any combination of compounds of Formula 202:

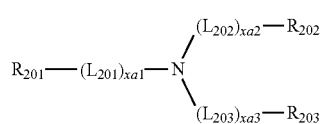

Formula 201

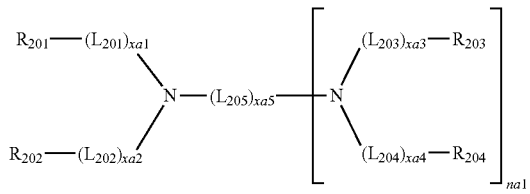

Formula 202 wherein, in Formulae 201 and 202, $L_{201}$ to $L_{204}$ are each, independently from one another, a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ is *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 are each, independently from one another, an integer from 0 to 5, xa5 is an integer from 1 to 10, $R_{201}$ to $R_{204}$ and $Q_{201}$ are each, independently from one another, a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, $R_{203}$ and $R_{204}$ are optionally linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, na1 is an integer from 1 to 4, and $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group each independently from one another, unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group each, independently from one another, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy so group; or a $C_3$-$C_{60}$ carbocyclic group, a $C_1$-$C_{60}$ heterocyclic group, a $C_7$-$C_{60}$ aryl alkyl group, or a $C_2$-$C_{60}$ heteroaryl alkyl group each, independently from one another, unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

9. The organic photodetector of claim 7, wherein an amount of the p-dopant in the first hole transport layer is about 0.1 vol. % to about 10 vol. %.

10. The organic photodetector of claim 1, wherein the first hole transport layer has a thickness of about 5 Å to about 150 Å.

11. The organic photodetector of claim 1, wherein the activation layer comprises: a p-type semiconductor layer including a p-type organic semiconductor; and an n-type semiconductor layer including an n-type organic semiconductor, and
the p-type semiconductor layer and the n-type semiconductor layer form a PN junction.

12. The organic photodetector of claim 1, wherein the activation layer comprises: a p-type semiconductor layer including a p-type organic semiconductor; and an n-type semiconductor layer including an n-type organic semiconductor, and
a mixed layer of the p-type organic semiconductor and the n-type organic semiconductor.

13. The organic photodetector of claim 12, wherein
the p-type organic semiconductor comprises SubPc, CuPc, DBP, or any combination thereof, and
the n-type organic semiconductor comprises C60 fullerene, C70 fullerene, or any combination thereof.

14. The organic photodetector of claim 1, wherein the organic photodetector has a dark current density of about $1 \times 10^{-4}$ mA/cm$^2$ or less when a reverse bias of −3V is applied.

15. The organic photodetector of claim 1, wherein the organic photodetector does not comprise an electron blocking layer between the first electrode and the activation layer.

16. The organic photodetector of claim 1, wherein the first electrode comprises an anode,
the second electrode comprises a cathode,
the organic photodetector further comprises an electron transport region between the activation layer and the second electrode, and
the electron transport region comprises a hole blocking layer, an electron transport layer, an electron injection layer, or any combination thereof.

17. The organic photodetector of claim 16, wherein the electron transport region comprises the hole blocking layer, the electron transport layer, and the electron injection layer arranged sequentially from the activation layer.

18. An electronic apparatus comprising the organic photodetector of claim 1.

19. The electronic apparatus of claim 18, further comprising a light-emitting device.

20. An electronic apparatus comprising:
a substrate comprising a light detection region and a light emission region;
an organic photodetector on the light detection region; and
a light-emitting device on the light emission region,
wherein the organic photodetector comprises: a first pixel electrode; a second electrode facing the first pixel electrode; and a hole injection layer, a hole transport layer, and an activation layer arranged sequentially between the first pixel electrode and the second electrode, wherein the hole transport layer comprises: a first hole transport layer including a p-dopant; and a second hole transport layer not including a p-dopant,
the light-emitting device comprises: a second pixel electrode; the second electrode facing the second pixel electrode; and the hole injection layer, the second hole transport layer, and an emission layer arranged sequentially between the second pixel electrode and the second electrode,
the first pixel electrode, the first hole transport layer, and the activation layer at least partially overlap the light detection region,
the second pixel electrode and the emission layer at least partially overlap the light emission region, and
the hole injection layer, the second hole transport layer, and the counter electrode overlap substantially the entirety of the light detection region and the light emission region.

* * * * *